United States Patent
Wakai

(10) Patent No.: US 9,865,048 B2
(45) Date of Patent: Jan. 9, 2018

(54) RADIOTHERAPY INFORMATION GENERATION APPARATUS AND RADIOTHERAPY INFORMATION GENERATION METHOD

(71) Applicant: Toshiba Medical Systems Corporation, Otawara-shi (JP)

(72) Inventor: Satoshi Wakai, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 75 days.

(21) Appl. No.: 14/179,093

(22) Filed: Feb. 12, 2014

(65) Prior Publication Data

US 2014/0161339 A1    Jun. 12, 2014

Related U.S. Application Data

(63) Continuation of application No. PCT/JP2012/072994, filed on Sep. 7, 2012.

(30) Foreign Application Priority Data

Sep. 15, 2011   (JP) .................................. 2011-201238

(51) Int. Cl.
   G06K 9/00      (2006.01)
   G06T 7/00      (2017.01)
   A61N 5/10      (2006.01)

(52) U.S. Cl.
   CPC ............ *G06T 7/0012* (2013.01); *A61N 5/103* (2013.01); *A61N 2005/1074* (2013.01)

(58) Field of Classification Search
   None
   See application file for complete search history.

(56) References Cited

U.S. PATENT DOCUMENTS 6,118,847 A * 9/2000 Hernandez-Guerra ............... A61B 6/541
                                                  250/505.1
7,831,289 B2  11/2010 Riker et al.
(Continued)

FOREIGN PATENT DOCUMENTS

CN      101015723 A      8/2007
JP      2003-117010      4/2003
(Continued)

OTHER PUBLICATIONS

MacManus, Michael, et al. "Use of PET and PET/CT for radiation therapy planning: IAEA expert report 2006-2007." Radiotherapy and oncology 91.1 (2009): 85-94.*

(Continued)

*Primary Examiner* — Sean Conner
(74) *Attorney, Agent, or Firm* — Oblon, McClelland, Maier & Neustadt, L.L.P.

(57) ABSTRACT

According to one embodiment, a radiotherapy information generation apparatus includes a region specific unit and a planning estimation unit. The region specific unit is configured to specify at least one area defined with respect to a tumor by analysis processing of diagnostic image data. The planning estimation unit is configured to display estimation information of planned dose values calculated based on the area and expected dose values of a radiation. Further, according to another embodiment, a radiotherapy information generation method includes specifying at least one area defined with respect to a tumor by analysis processing of diagnostic image data; and displaying estimation information of planned dose values calculated based on the area and expected dose values of a radiation.

17 Claims, 16 Drawing Sheets

(56) References Cited

U.S. PATENT DOCUMENTS

| | | | | |
|---|---|---|---|---|
| 2005/0111621 A1* | 5/2005 | Riker | ................... | A61N 5/1031 378/65 |
| 2008/0002811 A1* | 1/2008 | Allison | ................. | A61N 5/103 378/65 |
| 2012/0136194 A1* | 5/2012 | Zhang | ................... | A61N 5/103 600/1 |

FOREIGN PATENT DOCUMENTS

| | | |
|---|---|---|
| JP | 2006-043235 | 2/2006 |
| JP | 2008-080131 | 4/2008 |
| JP | 2008-178619 | 8/2008 |

OTHER PUBLICATIONS

Office Action dated Jun. 16, 2015 in Japanese Patent Application No. 2011-201238.

International Search Report dated Nov. 20, 2012 for PCT/JP2012/072994 filed on Sep. 7, 2012 with English Translation of Categories.

International Written Opinion dated Nov. 20, 2012 for PCT/JP2012/072994 filed on Sep. 7, 2012.

Combined Office Action and Search Report dated Feb. 2, 2015 in Chinese Patent Application No. 201280001249.3 (with English translation of categories of cited documents).

Translation of International Preliminary Report on Patentability and Written Opinion dated Mar. 27, 2014 in Application No. PCT/JP2012/072994.

Combined Chinese Office Action and Search Report dated Nov. 4, 2015 in Patent Application No. 201280001249.3 (with English language translation of categories of cited documents).

Office Action dated May 9, 2016, in Chinese Patent Application No. 201280001249.3 (with partial English-language translation).

Office Action dated Dec. 8, 2016, in Chinese Patent Application No. 201280001249.3.

Chinese Office Action dated Aug. 29, 2016 in Patent Application No. 201280001249.3.

Office Action dated Dec. 8, 2016 in Chinese Patent Application No. 201280001249.3.

* cited by examiner

| REGION | | PURPOSE OF TREATMENT | EXPECTED DOSE VALUE [Gy] |
|---|---|---|---|
| GTV | | PERMANENT CURE | 3 |
| | | SYMPTOM RELIEF | 3 |
| INVADED AREA (CTV - GTV) | | PERMANENT CURE | 3 |
| | | SYMPTOM RELIEF | 2 |
| SM | | PERMANENT CURE | 1 |
| | | SYMPTOM RELIEF | 0.5 |
| NORMAL TISSUE | | | 0.1 |

FIG. 7

RADIOTHERAPY INFORMATION GENERATION APPARATUS AND RADIOTHERAPY INFORMATION GENERATION METHOD

CROSS REFERENCES TO RELATED APPLICATIONS

This is a continuation of Application PCT/JP2012/72994, filed Sep. 7, 2012.

This application is based upon and claims the benefit of priority from Japanese Patent Application No. 2011-201238, filed Sep. 15, 2011; the entire contents of which are incorporated herein by reference.

FIELD

Embodiments described herein relate generally to a radiotherapy information generation apparatus and a radiotherapy information generation method.

BACKGROUND

The radiotherapy which treats a tumor by exposing radiation is conventionally known. The radiotherapy mainly includes three steps of acquiring diagnostic images by an image diagnostic apparatus, a radiation treatment planning, and the treatment by a radiation treatment apparatus.

Specifically, medical images are previously acquired in the radiotherapy for specifying a tumor area by an X-ray CT (calculated tomography) apparatus, an MRI (magnetic resonance imaging) apparatus, or a nuclear medicine diagnosis apparatuses such as a PET (positron emission calculated tomography) apparatus or a SPECT (single photon emission calculated tomography) apparatus.

Next, the radiation treatment planning is carried out. Specifically, the tumor to be treated and the normal tissues, to which an exposure of radiation is not desirable, are extracted from the medical images acquired by an image diagnostic apparatus. Subsequently, exposure conditions of radiation, such as an exposure range, a direction of exposure and an exposure intensity, are decided as a treatment plan based upon the extraction result. An exposure of radiation to the normal tissues cannot be avoided. Therefore, it is important to plan the exposure conditions of radiation so that an adverse effect does not arise as much as possible. For this reason, a radiation treatment planning requires analytical estimations, such as a DVH (Dose Volume Histogram), for estimating an adverse effect to the normal tissues and a curative effect as well as visual estimations with displaying a dose distribution on a medical image. The DVH is a graph showing a dose of radiation to each volume of a tumor tissue to be treated and the normal tissues.

In recent years, in order to decide upon more detailed conditions, a radiation treatment planning system which supports a radiation treatment planning is proposed. In the conventional radiation treatment planning system, anatomical information is defined based on medical images acquired by an image diagnostic apparatus, and exposure conditions of radiation, such as a direction of exposure, an exposure position, and a dose distribution, are calculated according to the defined anatomical information. Furthermore, the estimation of whether the calculated exposure conditions of radiation are appropriate is carried out.

For such a plan of the dose distribution of radiation and the like, the regions made by adding various margins to the tumor area have been defined conventionally. Specifically, the four regions of the GTV (Gross Tumor Volume), the CTV (Clinical Target Volume), the ITV (Internal Target Volume) and the PTV (Planning Target Volume) have been defined.

The GTV is a region judged that a tumor exists obviously by diagnosis of medical images. A portion in which a tumor invasion is suspected is also included in the GTV as long as it can be recognized on a medical image. The CTV is a region made by adding a minute invaded portion, which cannot be recognized on a medical image, to the GTV. The ITV is a target volume made by adding an IM (Internal Margin), which is a margin area in consideration of a movement of an organ, to the CTV. The PTV is a region made by adding an SM (Setup Margin) to the ITV three dimensionally in consideration of a degree in inaccuracy with regard to a positioning of a patient and a beam.

Then, the proper doses of radiations can be calculated for the respective tumor regions to which these margins have been added. For example, the exposure conditions of radiation can be set up so that a radiation having a sufficient dose not less than 95% may be exposed to not less than 99% of the CTV. Moreover, a model formula for calculating the margin to the PTV is also proposed. For example, a model formula for calculating the margin to the PTV required in order that the minimum dose in the CTV may exceed 95% of a prescribed dose in 90% of patients is known. Note that, in order to also include the periphery of the PTV in the 95% dose area, it is necessary to further add about 5 to $8 \times 10^{-3}$ [m] of a margin to the PTV to set up the exposure field of radiation.

After the exposure conditions of radiation has been decided upon as a radiation treatment planning by the dose calculation for every tumor area, it becomes possible to carry out a radiation treatment using a radiation treatment apparatus.

PRIOR TECHNICAL LITERATURE

[Patent literature 1] JPA2006-043235
[Patent literature 2] JPA2008-080131
[Patent literature 3] JPA2003-117010

However, there is a problem that the risk of adverse effect to a normal tissue increases since the regions with adding various margins to the tumor area to be treated are set in the radiation treatment planning. In particular, it is necessary to set up a different dose for every area according to a treatment purpose, such as a permanent cure or a symptom relief. However, each region, such as the invaded area by a tumor, is merely defined conceptually, and therefore, it cannot be set quantitatively.

As a result, even though a dose distribution of radiation is displayed in the radiation treatment planning, it is difficult to temporally or spatially grasp quantitive under exposure and over exposure areas of radiation with considering the invaded area. That is, there is a problem that an under exposure of radiation to the treatment target and an over exposure of radiation to normal tissues arise because it is difficult to quantitatively specify the exposure are of radiation such as the invaded area by a tumor.

Accordingly, it is an object of the present invention to provide a radiotherapy information generation apparatus and a radiotherapy information generation method which can generate radiotherapy information for reducing an over exposure and an under exposure of radiation in a radiotherapy.

BRIEF DESCRIPTION OF THE DRAWINGS

In the accompanying drawings:

FIG. 7 is a diagram showing an example of the expected dose values of radiation input into the dose calculation part shown in FIG. 1;

DETAILED DESCRIPTION

In general, according to one embodiment, a radiotherapy information generation apparatus includes a region specific unit and a planning estimation unit. The region specific unit is configured to specify at least one area defined with respect to a tumor by analysis processing of diagnostic image data. The planning estimation unit is configured to display estimation information of planned dose values calculated based on the area and expected dose values of a radiation.

Further, according to another embodiment, a radiotherapy information generation apparatus includes a region specific unit and a dose calculation unit. The region specific unit is configured to specify a gross tumor volume and an invaded area of a tumor by analysis processing of diagnostic image data. The dose calculation unit is configured to calculate planned dose values based on the gross tumor volume, the invaded area of the tumor and expected dose values of a radiation.

Further, according to another embodiment, a radiotherapy information generation method includes specifying at least one area defined with respect to a tumor by analysis processing of diagnostic image data; and displaying estimation information of planned dose values calculated based on the area and expected dose values of a radiation.

A radiotherapy information generation apparatus and a radiotherapy information generation method according to embodiments of the present invention will be described with reference to the accompanying drawings.

Figure 1:
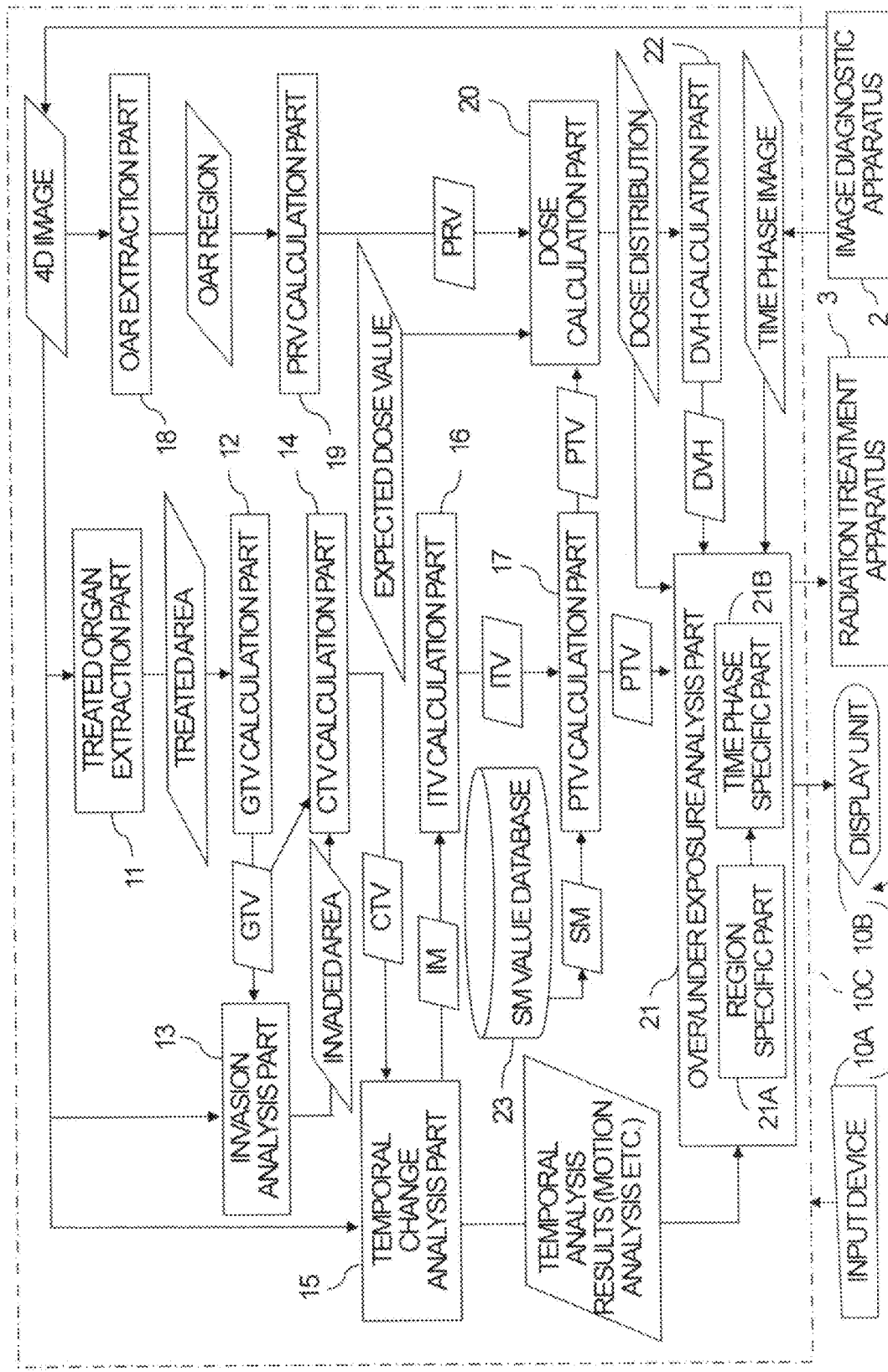
FIG. 1 is a functional block diagram of a radiotherapy information generation apparatus according to an embodiment of the present invention.
Figure 2:
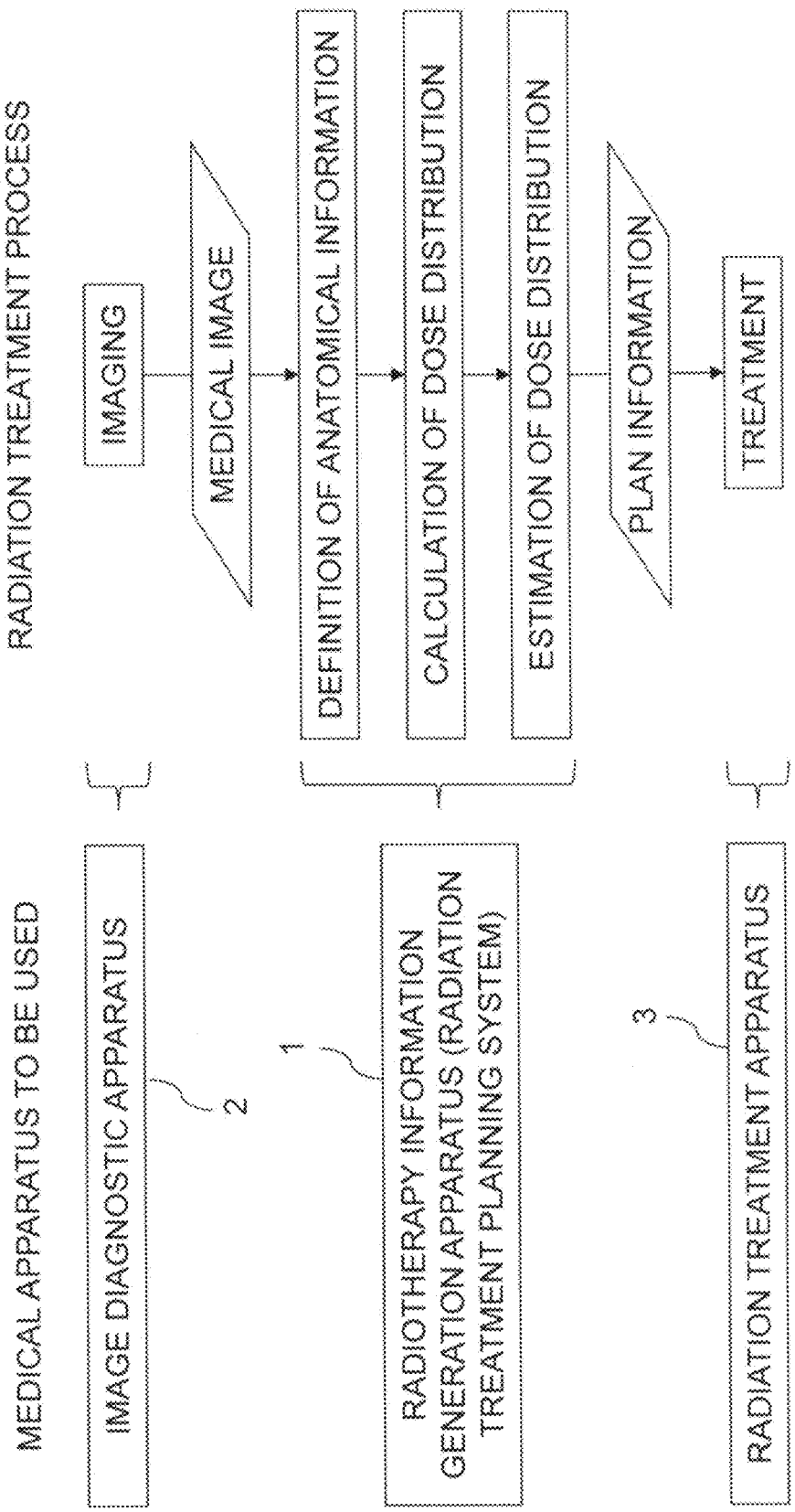
FIG. 2 is a diagram showing medical apparatuses used with the radiotherapy information generation apparatus 1 shown in FIG. 1 in radiotherapy and a flow of the radiotherapy.

FIG. 1 is a functional block diagram of a radiotherapy information generation apparatus according to an embodiment of the present invention and FIG. 2 is a diagram showing medical apparatuses used with the radiotherapy information generation apparatus 1 shown in FIG. 1 in radiotherapy and a flow of the radiotherapy.

As shown in FIG. 2, the process of radiotherapy roughly consists of three steps of acquisition of medical images by an image diagnostic apparatus 2, a radiation treatment planning, and a radiation treatment by a radiation treatment apparatus 3. More specifically, acquisition of medical images including a tumor part of a patient is performed in the image diagnostic apparatus 2. Next, the radiation treatment planning based on the acquired medical images is carried out in the radiotherapy information generation apparatus 1. That is, the definition of anatomical information based on the medical images, the calculation of dose distribution of radiation based on the defined anatomical information and the estimation of the dose distribution calculated as the radiation treatment planning are performed. Then, the radiation treatment of the patient is carried out using the radiation treatment apparatus 3 according to the plan information including the dose distribution decided upon in the radiation treatment planning.

The radiotherapy information generation apparatus 1 has a function as a radiation treatment planning system for the radiation treatment planning in radiotherapy. As shown in FIG. 1 and FIG. 2, the case where the radiotherapy information generation apparatus 1 is independent of the image diagnostic apparatus 2 and the radiation treatment apparatus 3 is explained here. However, the radiation treatment planning system may be built in the image diagnostic apparatus 2 or the radiation treatment apparatus 3. In that case, the image diagnostic apparatus 2 or the radiation treatment apparatus 3 having the function as the radiation treatment planning system serves as the radiotherapy information generation apparatus 1.

When the radiotherapy information generation apparatus 1 is the radiation treatment planning system which is independent of the image diagnostic apparatus 2 and the radiation treatment apparatus 3, the radiotherapy information generation apparatus 1 is connected with the image diagnostic apparatus 2 and the radiation treatment apparatus 3 through a network. Note that, the radiotherapy information generation apparatus 1 may be connected with the image diagnostic apparatus 2 and the radiation treatment apparatus 3 through medical devices, such as a medical image server and/or a medical image processing apparatus.

The image diagnostic apparatus 2 is used in order to acquire diagnostic images of a patient, including a tumor region which is the target of radiotherapy, for the radiation treatment planning. Examples of the image diagnostic apparatus 2 used in the radiotherapy include an X-ray CT apparatus, an MRI apparatus, or a nuclear medicine diagnosis apparatuses such as a PET apparatus or a SPECT apparatus. Note that, diagnostic images for the radiation treatment planning may be acquired by plural image diagnostic apparatuses 2 like a PET apparatus and an X-ray CT apparatus. Moreover, unified image diagnostic apparatuses 2 like a PET/CT apparatus may be used.

The radiotherapy information generation apparatus 1 is an apparatus which generates the exposure conditions of radiation, such as a dose distribution of radiation, as the radiation treatment planning information based on diagnostic image data including the tumor part acquired by the image diagnostic apparatus 2. The radiotherapy information generation apparatus 1 can be configured by installing program into an operation unit 10C of a computer 10 equipped with an input device 10A and a display unit 10B.

Specifically, the operation unit 10C of the radiotherapy information generation apparatus 1 functions as a treated organ extraction part 11, a GTV calculation part 12, an invasion analysis part 13, a CTV calculation part 14, a temporal change analysis part 15, an ITV calculation part 16, a PTV calculation part 17, an OAR extraction part 18, a PRV calculation part 19, a dose calculation part 20, an over/under exposure analysis part 21, and a DVH calculation part 22. Furthermore, the over/under exposure analysis part 21 has a region specific part 21A and a time phase specific part 21B. Moreover, the storage unit can be operated as an SM value database 23. However, in order to prepare a part or all of these functions, circuits may be used for configuring the radiotherapy information generation apparatus 1.

The radiation treatment apparatus 3 is an apparatus for performing the radiation treatment according to the exposure conditions of radiation made by the radiotherapy information generation apparatus 1. Specifically, the radiation treatment apparatus 3 can consist of an X-ray diagnostic apparatuses which exposes an X-ray to an object as a patient.

Next, a flow of the radiotherapy and the detailed functions of the radiotherapy information generation apparatus 1 will be described with reference to FIG. 1 and FIG. 2.

First, the object which is a patient is set to the bed of the image diagnostic apparatus 2, and positioning of the object is carried out with acquisition of locator images. Then, diagnostic image data which include a tumor part from the object are acquired. Examples of the diagnostic image data for the radiation treatment planning include a combination of 3D (three dimensional) X-ray CT image data and 3D TOF (time of flight)-PET image data, a combination of 4D (four dimensional) X-ray CT image data and 4D TOF-PET image data, and MR image data.

In case of acquiring 4D-CT image data and 4D-PET image data, imaging of the object is performed by an united PET/CT apparatus, or an X-ray CT apparatus and a PET apparatus which are mutually independent. When the object is imaged using an X-ray CT apparatus and a PET apparatus which are mutually independent, rigid positioning processing and non-rigid positioning processing are needed between X-ray CT image data and PET image data. On the other hand, using a PET/CT apparatus makes it possible to acquire both X-ray CT image data and PET image data by a single scan. When a PET/CT apparatus is used, it is not always necessary to perform positioning processing between X-ray CT image data and PET image data. However, it is sometimes desired to correct a local position gap between X-ray CT image data and PET image data by non-rigid positioning processing in order to perform an image analysis with a high precision in the radiation treatment planning.

The treated organ extraction part 11 of the radiotherapy information generation apparatus 1 acquires the diagnostic image data of the object, from the image diagnostic apparatus 2 directly or indirectly through a medical image server and/or a medical image processing apparatus, for the radiation treatment planning. Then, the treated organ extraction part 11 extracts an organ, to which a radiation should be exposed, as a target of the radiation treatment, from the diagnostic image data.

The extraction of the organ to be treated can be performed automatically by known region extraction processing such as threshold processing with regard to pixel value with reference to an organ atlas and/or outline extraction processing. Moreover, the treated organ automatically extracted may be adjusted by operation of the input device 10A. When it is difficult to automatically extract the treated organ as a region, the treated organ can be specified manually or semi automatically by inputting information for specifying the treated organ from the input device 10A. In this case, the diagnostic image data, such as X-ray CT image data, depicting the form of the organ are referred to. Then, the treated organ can be specified on the diagnostic image data based on known anatomical information including the form and position of the organ, and values of image signals.

Next, the GTV calculation part 12 calculates a GTV based on the treated organ extracted by the treated organ extraction part 11. The GTV is a tumor region in which it is determined that a tumor exists clearly based on the diagnostic image data. For example, the region in which the organ to be treated lies can be set to the GTV. Moreover, the GTV can be also automatically calculated as a tumor region by threshold processing with regard to the pixel values of the treated organ extracted by the treated organ extraction part 11. Alternatively, information for specifying a region in which the tumor has been recognized with reference to the diagnostic image data displayed on the display unit 10B may be input into the GTV calculation part 12 from the input device 10A so that the GTV calculation part 12 can determine the GTV according to the information for specifying the tumor region. That is, the GTV can be determined automatically by image processing, such as threshold processing to pixel values, or manually according to the information input from the input device 10A.

Next, the invasion analysis part 13 acquires a single kind or multi kinds of diagnostic image data, having mutually different contrasts, from the image diagnostic apparatus 2, and automatically specifies an invaded area by the tumor with analysis processing including threshold processing of the single kind or the multi kinds of the diagnostic image data. The invaded area is a tumor portion which cannot be recognized with the naked eye on the diagnostic image data. When the diagnostic image data are dynamic image data in time series, the invaded area can be specified for each time phase. Note that, in order to specify the invaded area, the GTV specified in the GTV calculation part 12 can be referred to.

The kinds of the diagnostic image data are determined so that the invaded area can be specified by threshold processing. Typically, the combination of 4D-CT image data and TOF-PET image data, dual energy image data which can be acquired with an X-ray CT apparatus, and the combination of PET image data and at least one of longitudinal relaxation (T1) weighted image (T1WI) data, transverse relaxation (T2) weighted image (T2WI) data and diffusion weighted image (DWI) data which can be acquired by MRI are exemplified. Note that, the dual energy image uses a difference in the attenuation coefficient of a substance between average energies of X-ray and is generated based on a difference in the attenuation coefficient between mutually different X-ray energy bands.

Here, the case where plural invaded areas in time series are specified based on the combination of 4D X-ray CT image data and TOF-PET image data will be described as an example.

Figure 3:
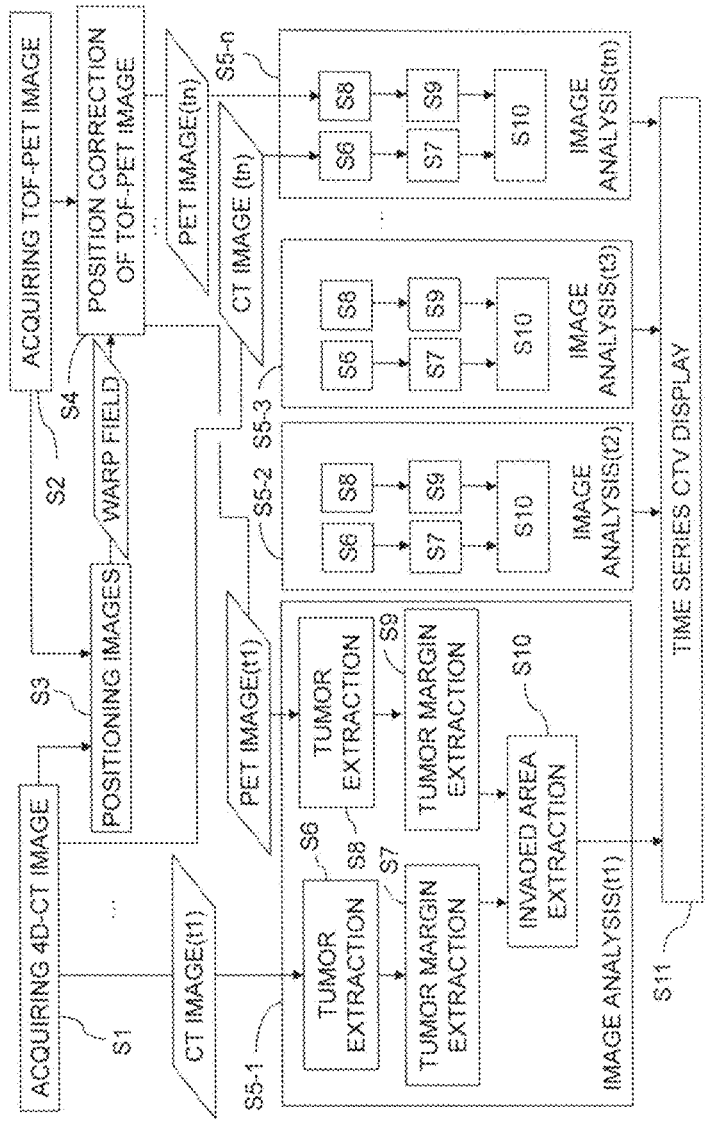
FIG. 3 is a flow chart showing an example of the flow of the invasion analysis carried out in the invasion analysis part shown in FIG. 1.

FIG. 3 is a flow chart showing an example of the flow of the invasion analysis carried out in the invasion analysis part 13 shown in FIG. 1.

First, in step S1, 4D-CT image data in time series are dynamically acquired by an X-ray CT apparatus. Thereby, 3D-CT image data corresponding to time phases t1, t2, t3, . . . , tn are acquired sequentially.

On the other hand, in step S2, TOF-PET image data in time series are dynamically acquired as 4D image data by a PET apparatus. Thereby, n (n is a natural number) frames of TOF-PET image data corresponding to the time phases t1, t2, t3, . . . , tn are acquired sequentially.

Next, in step S3, non-rigid positioning processing between the 4D-CT image data acquired by the X-ray CT apparatus and the TOF-PET image data acquired by the PET apparatus is performed by either the X-ray CT apparatus or the PET apparatus. Then, nonlinear position gaps between the 4D-CT image data and the TOF-PET image data are calculated as the result of the non-rigid positioning processing. The nonlinear position gaps can be expressed by a combination of parallel translation and deformation movement. Moreover, quantities of the deformation movement can be calculated by extraction of feature points and based on distances between the extracted feature points. The calculated position gaps can be expressed by data referred to as Warp Field which is a set of vectors, for example.

Next, in step S4, nonlinear position gap correction processing of the TOF-PET image data is performed based on the Warp Field which is the position gaps obtained as the result of the non-rigid positioning processing. Thereby, TOF-PET image data after the position correction corresponding to the time phases t1, t2, t3, . . . , tn are generated.

Next, in step S5-1 to step S5-n, an image analysis based on the 3D-CT image data and the TOF-PET image data after the position correction each corresponding to the time phases t1, t2, t3, . . . , tn are performed in the invasion analysis part 13.

Specifically, in step S6, the invasion analysis part 13 extracts a tumor area automatically by threshold processing of the 3D-CT image data. Next, in step S7, the invasion analysis part 13 extracts peripheral areas of the tumor, each considered to be a tumor invaded portion, by threshold processing of the 3D-CT image data. On the other hand, in step S8, the invasion analysis part 13 extracts a tumor area automatically by threshold processing of the TOF-PET image data. Next, in step S9, the invasion analysis part 13 extracts peripheral areas of the tumor, each considered to be a tumor invaded portion, by threshold processing of the TOF-PET image data.

The threshold values for these threshold processings can be set as experiential values or scientifically reported values. Note that, the tumor area may be one extracted by the GTV calculation part 12 for specifying the GTV.

Next, in step S10, the invasion analysis part 13 specifies an invaded area by the tumor based on the tumor area and the tumor peripheral areas extracted from the 3D-CT image data, and the tumor area and the tumor peripheral areas extracted from the TOF-PET image data. For example, an area including the respective tumor peripheral areas outside the tumor area, a common area of the respective tumor peripheral areas outside the tumor area, or a middle area thereof can be extracted as the invaded area.

The image analyses from step S6 to step S10 are performed for each time phase based on the 3D-CT image data and the TOF-PET image data after the position correction corresponding to the time phases t1, t2, t3, . . . , tn.

When the invaded area has been specified, the CTV calculation part 14 calculates the CTV by adding the invaded area to the GTV acquired from the GTV calculation part 12. The CTV is an area made by adding minute invaded portions, which cannot be recognized visually on a diagnostic image, to the GTV. Therefore, the CTV is a target area, to which the radiation is exposed, including the invaded area as a margin.

When frames of image data in time series have been acquired as diagnostic image data as shown in FIG. 3, the CTVs in time series corresponding to the time phases t1, t2, t3, . . . , tn are obtained. In this case, in step S11, the CTV calculation part 14 can display the CTVs in time series on the display unit 10B.

On the other hand, specifying the invaded area based on DWI data and PET image data will be explained as another example.

Figure 4:
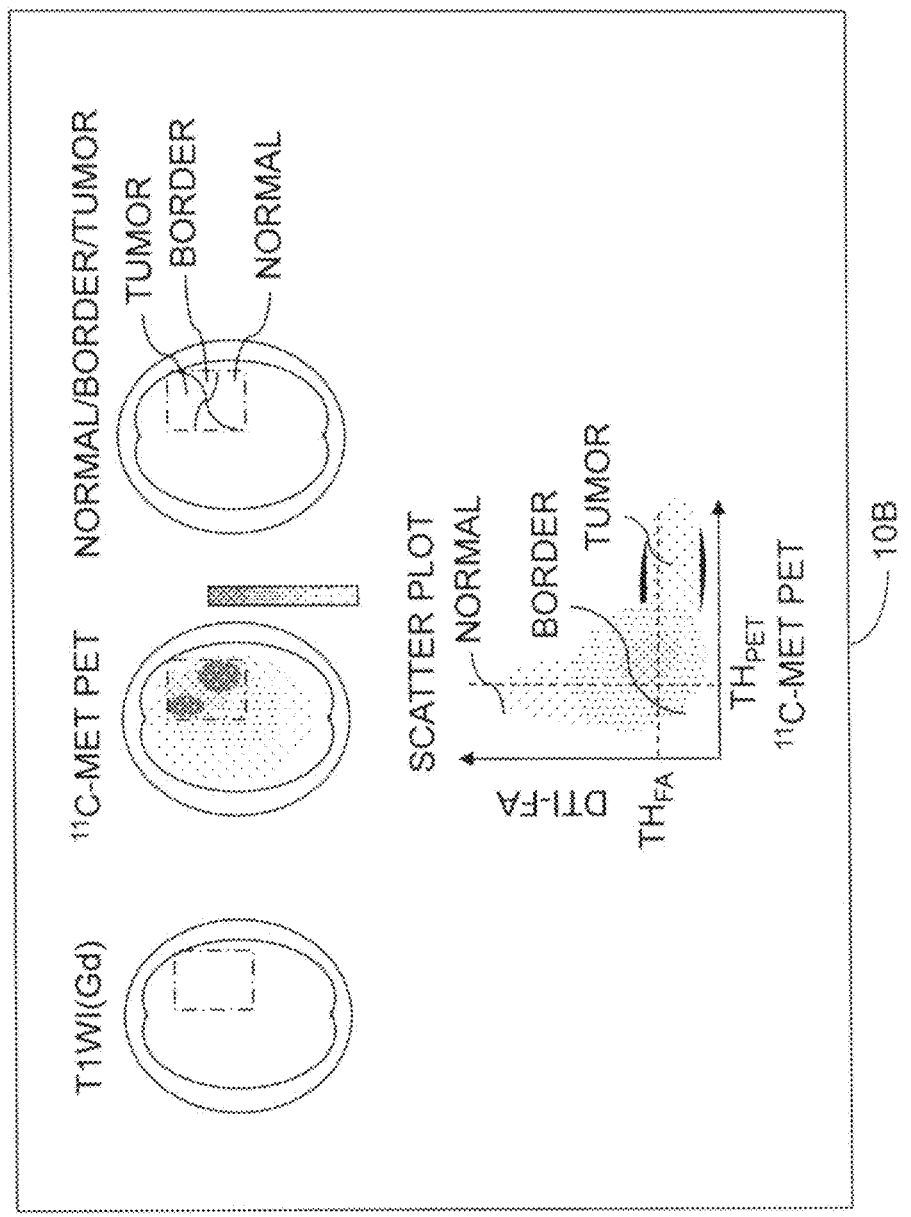
FIG. 4 is a diagram showing an example of displaying an analysis result in another example of the invasion analysis carried out in the invasion analysis part shown in FIG. 1 with diagnostic image data.

FIG. 4 is a diagram showing an example of displaying an analysis result in another example of the invasion analysis carried out in the invasion analysis part 13 shown in FIG. 1 with diagnostic image data.

When DWIs acquired with applying MPG (motion probing gradient) pulses having mutually different intensities or application directions in an MRI apparatus are analyzed, DTI (diffusion tensor image) data and FA (Fractional Anisotropy) data as 2D (two dimensional) parameter image data are obtained. On the other hand, when imaging is performed by a PET apparatus with injecting methionine in which carbon C11 emitting a radiation has been added, 11C-MET PET image data is acquired.

Then, a 2D map of which two axes are the respective signal intensities of the FA data and the 11C-MET PET image data can be created in the invasion analysis part 13. FIG. 4 shows an example of displaying a created 2D map of the FA data and the 11C-MET PET image data together with corresponding diagnostic images on the display unit 10B.

That is, the T1WI acquired by the MRI apparatus and the 11C-MET PET image acquired by the PET apparatus are displayed as the diagnostic images. Note that, the T1WI is a contrast-enhanced MR image obtained by injecting gadolinium as a contrast agent. The T1WI is usually displayed as brightness with a gray scale while the 11 C-MET PET image can be displayed by colors according to image signal values with a color scale. On these diagnostic images, a ROI (region of interest) as shown by a dashed line can be set according to values of image signals.

Then, by creating the 2D map of the FA data and the 11C-MET PET image data using the image signals in the ROI, it becomes possible to classify the 2D map into the normal tissues, the invaded areas, and the tumor area visually by threshold processing of the respective signal intensities of the FA data and the 11C-MET PET image data. That is, the invaded areas by the tumor can be specified based on the combination of the FA data and the PET image data.

Specifically, an area which consists of a group of points each showing an image signal larger than a threshold value $TH_{FA}$ set to the FA data and an image signal not more than a threshold value $TH_{PET}$ set to the 11C-MET PET image data can be classified as the normal area. Further, an area which consists of a group of points each showing an image signal not more than the threshold value $TH_{FA}$ set to the FA data and an image signal not more than the threshold value $TH_{PET}$ set to the 11C-MET PET image data can be classified as the invaded area. Furthermore, an area which consists of a group of points each showing an image signal not more than the threshold value $TH_{FA}$ set to the FA data and an image signal larger than the threshold value $TH_{PET}$ set to the 11C-MET PET image data can be classified as the tumor area.

That is, the normal tissues, the invaded areas, and the tumor area can be specified by threshold processing of each signal intensity of the FA data and the 11C-MET PET image data. The classified normal tissues, invaded areas, and tumor area can be displayed on a diagnostic image using mutually different colors or the like so that they can be distinguished. FIG. 4 shows an example of displaying the normal tissues, the invaded areas, and the tumor area on a T1WI so that they can be distinguished.

Then, the invaded areas specified in this way are given to the CTV calculation part 14. Thereby, the CTV calculation part 14 can add the invaded areas to the GTV to calculate the CTV.

On the other hand, the temporal change analysis part 15 calculates the IM, which is a margin area representing a moving distance of an organ, based on the 4D diagnostic image data in the time series acquired from the image diagnostic apparatus 2 and the CTV acquired from the CTV calculation part 14 automatically or semi automatically with reference to information from the input device 10A, as needed. For example, a movable range of the CTVs, outside the CTV in a specific time phase, in other time phases can be set to the IM.

Next, the ITV calculation part 16 automatically calculates the ITV which is the target volume made by adding the IM to the CTV. For example, a movable range of the CTVs in the time series at the respective time phases can be automatically calculated as the ITV.

Figure 5:
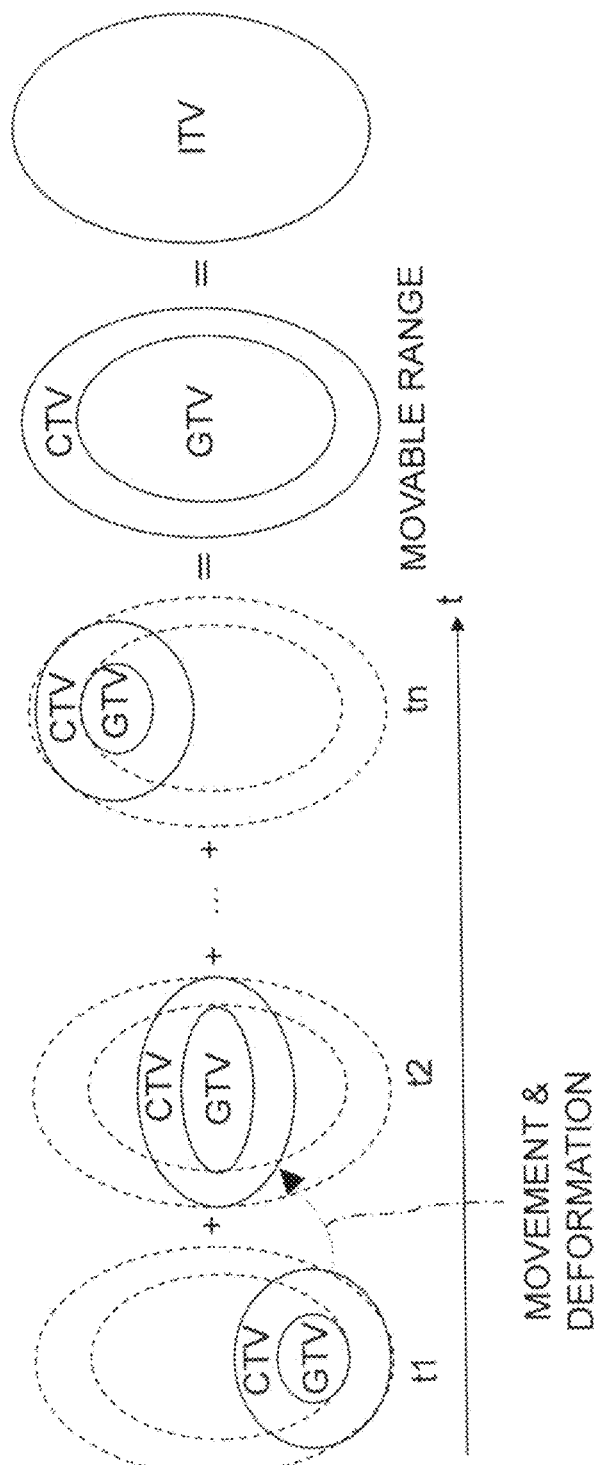
FIG. 5 is a diagram conceptually showing an example of method for calculating the ITV in the ITV calculation part shown in FIG. 1.

FIG. 5 is a diagram conceptually showing an example of method for calculating the ITV in the ITV calculation part 16 shown in FIG. 1.

As shown in FIG. 5, the GTV calculation part 12 and the CTV calculation part 14 respectively calculate the GTVs and the CTVs at the respective time phases t1, t2, t3, . . . , tn. Since the organ to be treated moves and deforms between the time phases as shown in FIG. 5, the GTV and the CTV change for each time phase. Accordingly, moving and deforming ranges of the GTV and the CTV can be respectively set to the GTV and the CTV which do not depend on the time phases. Further, the CTV which does not depend on the time phases, i.e., the movable range of the CTV can be set to the ITV as it is.

In this case, the movable ranges of the GTV and the CTV can be automatically calculated as the IM and the ITV respectively by projecting the GTVs and the CTVs at the respective time phases t1, t2, t3, . . . , tn in the time phase direction, for example. However, at least one of the IM and the ITV may be automatically calculated based on motion information acquired as a result of a movement analysis, such as a WMT (Wall Motion Tracking) of a myocardium, or a Warp Field calculated as a set of movement vectors by non-rigid positioning processing, as well as the projection processing in the time axis direction. Note that, the WMT is a technique for analyzing a wall movement of a myocardium by a twisting analysis and an analysis result can be obtained by the image diagnostic apparatus 2 such as an MRI apparatus.

However, there is a possibility that an excess radiation is exposed to the normal area outside the part to be treated at a specific time phase depending on a relative relation between the sizes of the movable ranges of the GTV and the CTV and the normal portion if the movable range of the CTV is set to the ITV as it is. Accordingly, when the radiation treatment planning using the radiation treatment apparatus 3, such as a cyber knife, allowing temporally adjusting the exposed area of radiation is performed, the CTVs in the time series corresponding to the respective time phases may be set to the ITVs in the time series corresponding to the respective time phases as they are.

Next, the PTV calculation part 17 adds the SM, input from the input device 10A as an index representing the degree in inaccuracy of the positioning between a patient and a radiation beam, to the ITV calculated in the ITV calculation part 16. Thereby, the PTV which is defined as the volume made by adding the SM to the ITV is calculated.

Note that, the SM value varies depending on conditions of preprocessing till the PTV is calculated. The conditions which influence the SM value include an organ extraction algorithm used for the extraction of the organ to be treated, the kind of organ to be treated, and the kind of image diagnostic apparatus 2 used for the acquisition of the diagnostic images. Accordingly, the SM values previously related to these conditions can be stored in the SM value database 23. In this case, by selecting a condition by operation of the input device 10A, the corresponding SM value can be input into the PTV calculation part 17.

By the calculation of the PTV, specifying the tumor areas normally defined with regard to a tumor is completed. Between the respective tumor areas GTV, CTV, ITV, and PTV, the relations expressed by the formulas (1-1), (1-2), and (1-3) are satisfied.

$$GTV \leq CTV \leq ITV < PTV \qquad (1\text{-}1)$$

$$ITV = CTV + IM \qquad (1\text{-}2)$$

$$PTV = ITV + SM \qquad (1\text{-}3)$$

Figure 6:
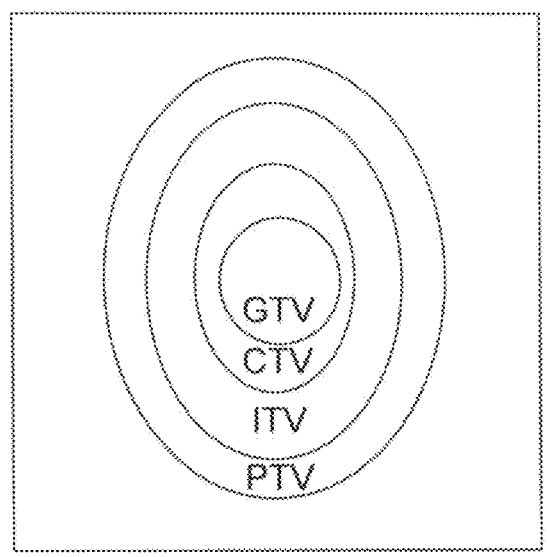
FIG. 6 is a schematic diagram expressing the relation between the respective tumor areas specified in the radiotherapy information generation apparatus shown in FIG. 1.

FIG. 6 is a schematic diagram expressing the relation between the respective tumor areas specified in the radiotherapy information generation apparatus 1 shown in FIG. 1. As shown in FIG. 6, the ITV is to be set inside the PTV, the CTV is to be set inside the ITV, and the GTV is to be set inside the CTV.

On the other hand, the OAR extraction part 18 acquires the diagnostic image data from the image diagnostic apparatus 2 and extracts an OAR (Organ at risk) by subjecting the diagnostic image data image processing similar to that for the extraction of the organ to be treated.

Next, the PRV calculation part 19 calculates the PRV (Planning organ at risk volume) based on the OAR area by a method similar to the calculation of the PTV. That is, the PRV is calculated by adding the margin area, in consideration of the temporal movement, deformation, and degree in inaccuracy of the OAR, to the OAR area.

Next, the dose calculation part 20 calculates a planned dose value based on the respective expected dose values of the radiation to the tumor areas, input according to a treatment purpose from the input device 10A, the PRV and the PTV. Specifically, the planned dose value can be calculated based on the expected dose values of the radiation individually set up to the tumor areas including the GTV and the invaded areas by the tumor. For example, the planned dose value can be calculated based on the GTV, the invaded areas by the tumor, the expected dose value of the radiation set up to the GTV, and the expected dose value of the radiation set up to the invaded areas by the tumor.

FIG. 7 is a diagram showing an example of the expected dose values of radiation input into the dose calculation part 20 shown in FIG. 1.

As shown in FIG. 7, the expected dose values of the radiation are set as mutually different ideal values according to the treatment purposes and the treated areas including the margins. For example, the expected dose value is set so as to vary depending on whether the treatment purpose is the permanent cure or the symptom relief. Moreover, the expected dose values can be also set up to the PRV. Since the PTV is the treated target, a sufficient dose is set up as the expected value. On the contrary, to the PRV to which the exposure of radiation is not desirable, the expected value is set up as a super low dose or so that the radiation may not be exposed.

When such expected dose values have been input into the dose calculation part 20, the dose calculation part 20 calculate a dose distribution by a known method, such as a simulation using the Monte Carlo method or a solution of the inverse problem. However, the direction in which the radiation can be exposed and the accuracy differ according to each radiation treatment apparatus 3. Therefore, it is desirable on accuracy for the dose calculation part 20 to calculate the dose distribution on conditions of the characteristics of the radiation treatment apparatus 3 used for the radiation treatment by inputting parameters representing the characteristics of the radiation treatment apparatus 3 from the input device 10A into the dose calculation part 20.

Next, the over/under exposure analysis part 21 compares the dose distribution calculated as the planned dose values by the dose calculation part 20 with the expected dose values to specify over exposure areas, under exposure areas, over exposure time phases, and under exposure time phases of the radiation. Specifically, the region specific part 21A compares the planned dose values with the expected dose values for every time phase to specify the over exposure areas and the under exposure areas of the radiation. Moreover, the time phase specific part 21B specifies the time phases, at which at least one of the over exposure area and the under exposure area exists, as one or both of the over exposure time phases and the under exposure time phases based on the comparison result by the region specific part 21A.

Next, the over/under exposure analysis part 21 displays at least one of the differences between the planned dose values and the expected dose values of the radiation, the over exposure areas, the under exposure areas, the over exposure time phases, and the under exposure time phases on the display unit 10B as estimation information to the planned dose values.

Figure 8:
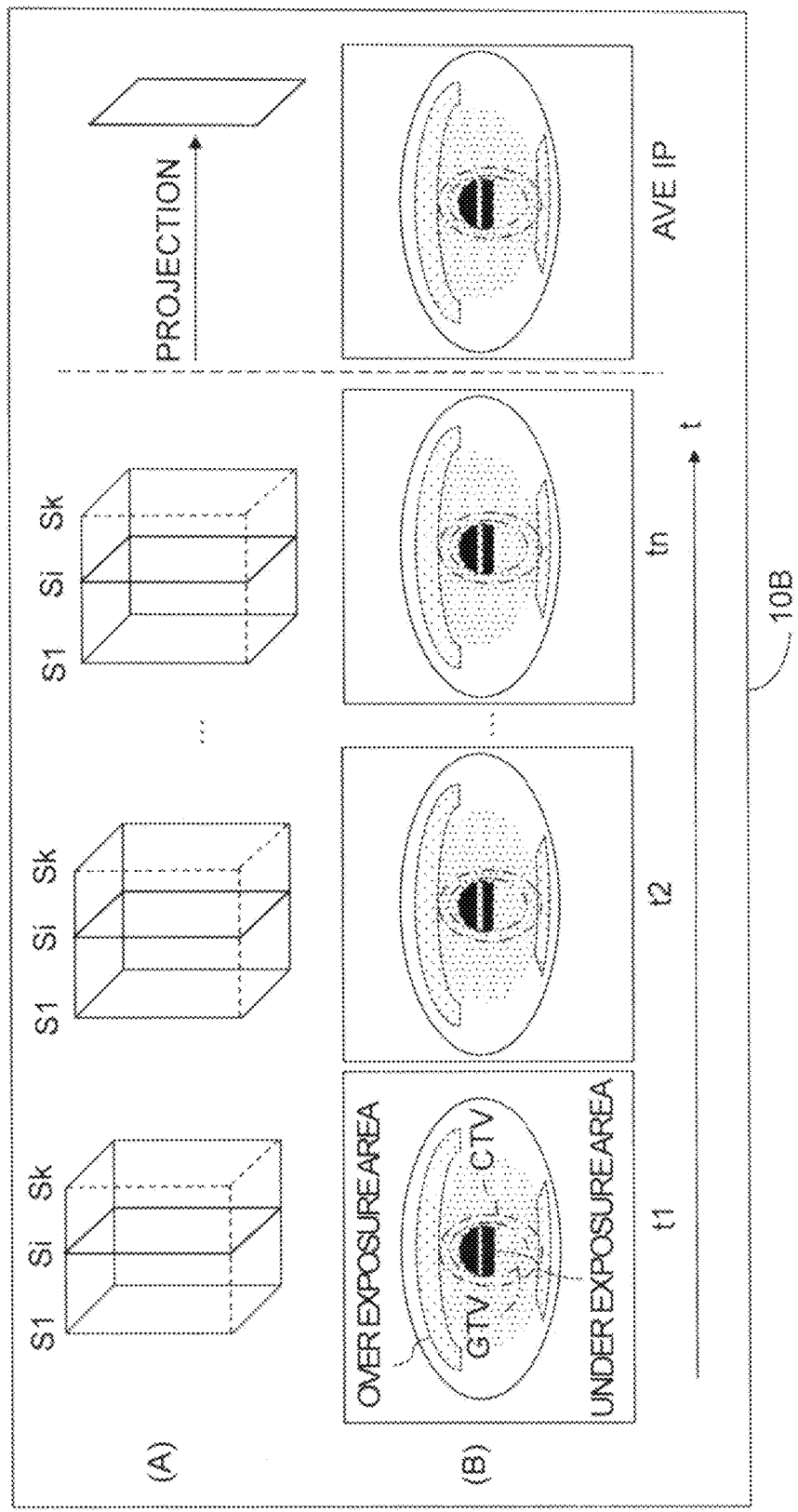
FIG. 8 is a diagram showing an example of displaying over exposure areas and under exposure areas specified by the over/under exposure analysis part shown in FIG. 1 for every time phase.

FIG. 8 is a diagram showing an example of displaying over exposure areas and under exposure areas specified by the over/under exposure analysis part 21 shown in FIG. 1 for every time phase.

From multi slice image data in the time series at k (k is a natural number) slices S1, S2, S3, . . . , Sk as shown in FIG. 8 (A), 2D image data at the appropriate i-th slice Si can be extracted. Then, the 2D over exposure areas and the 2D under exposure areas of the radiation at the same slice position can be displayed in the time series on the display unit 10B as shown in FIG. 8 (B).

In the example of FIG. 8 (B), the ranges of the GTV and the CTV, including the invaded area as the margins, are displayed together with the differences between the planned dose values and the expected dose values on 2D tomographic images at the respective time phases t1, t2, t3, . . . , tn. The 2D distribution consisting of the differences between the planned dose values and the expected dose values can be visually displayed using colors, for example. Furthermore, the over exposure areas and the under exposure areas of the radiation can be displayed emphatically using colors or the like based on the differences between the planned dose values and the expected dose values.

Consequently, the propriety of the dose distribution set up as the planned dose values in the GTV and the CTV can be judged easily. Moreover, displaying worsen parts, such as the GTV and the CTV, preferentially instead of all the tumor areas makes it possible to grasp the over exposure areas and the under exposure areas easily.

Although the GTV, the CTV, the differences between the planned dose values and the expected dose values, the over exposure areas, and the under exposure areas have been displayed on the 2D tomographic images in FIG. 8 (B), they may be displayed on other 2D images. For example, the GTV, the CTV, the over exposure areas, and the under exposure areas may be superimposed and displayed on MPR (multi planar reconstruction) images, VR (volume rendering) images, SR (surface rendering) images, IP (Intensity Projection) images including MIP (Maximum Intensity Projection) images and MinIP (Minimum Intensity Projection) images, or 2D images, such as Curved MPR images, used for displaying general volume image data. Furthermore, plural medical images acquired by two or more image diagnostic apparatuses 2 may be fusion-displayed mutually.

Moreover, the 2D images corresponding to the time phases t1, t2, t3, . . . , tn at the same slice Si may be projected in the time phase direction to generate an average intensity projection (Ave IP) image as shown in FIG. 8. Thereby, it may become possible to compare the planned dose distribution with the spatial relationship of organs easily since the organs each showing high image signal values can be displayed emphatically.

Figure 9:
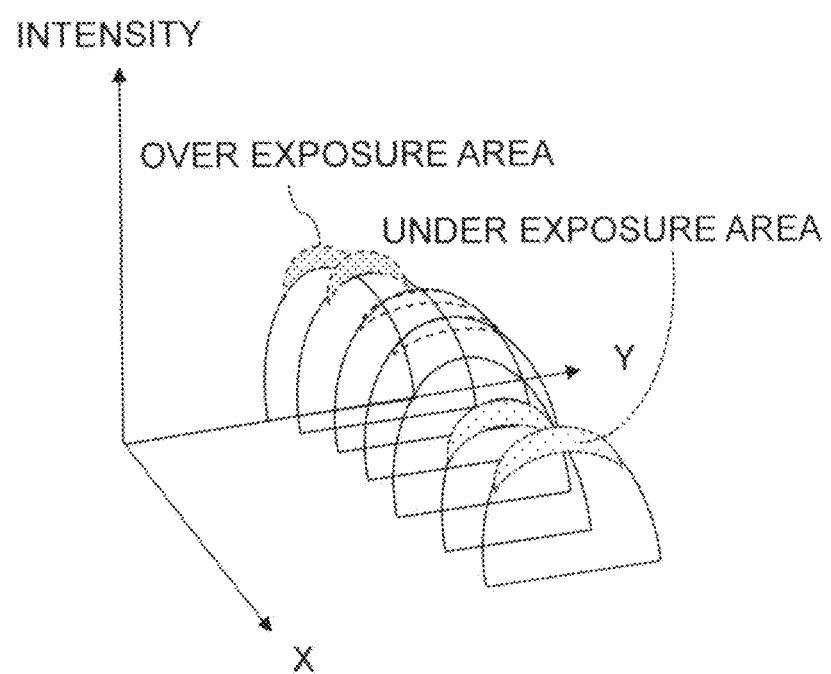
FIG. 9 is a diagram showing an example of three dimensionally displaying over exposure areas and under exposure areas specified by the over/under exposure analysis part shown in FIG. 1.

FIG. 9 is a diagram showing an example of three dimensionally displaying the over exposure areas and the under exposure areas specified by the over/under exposure analysis part 21 shown in FIG. 1.

As shown in FIG. 9, the over exposure areas and the under exposure areas may be also displayed three dimensionally. FIG. 9 shows an example of displaying the over exposure areas and the under exposure areas on a Beam's eye view, which shows intensities of the radiation at 2D positions (X, Y) of the treated area, so that the over exposure areas and the under exposure areas can be distinguished. Specifically, the differences between the 3D distribution of the expected dose values and the 3D distribution of the planned dose values can be displayed. In addition, the over exposure areas and under exposure areas of the radiation can be displayed emphatically using colors or the like.

Otherwise, the GTV, the CTV, the differences between the planned dose values and the expected dose values, the over exposure areas, and the under exposure areas may be displayed on an analysis image representing a result of motion analysis, such as the Warp Field acquired as a result of non-rigid positioning processing or a WMT of the myocardium. In this case, displaying the ITV makes it possible to compare the ITV with the dose distribution easily.

Thus, desired information, such as the tumor areas including the GTV, the margin regions including the invaded areas, the OAR, the PRV, the dose distribution, the differences between the planned dose values and the expected dose values, the over exposure areas, and the under exposure areas, can be superimposed and displayed two dimensionally or three dimensionally on 2D images displayed as reference images on the display unit 10B by display processing in the over/under exposure analysis part 21. Thereby, it becomes possible to judge the propriety of the planned dose values with viewing the features of organs.

Each image displayed on the display unit 10B can be also used as an interface for a resetting of the exposure conditions of the radiation. For example, a region can be designated by use of the input device 10A, such as a mouse, so that the expected dose values in the designated region are changed locally. Moreover, it is possible to change the expected dose values themselves. Similarly, it is also possible to adjust the margin areas and the tumor areas, such as the CTV.

That is, the over/under exposure analysis part 21 can display desired information, such as the tumor areas including the GTV, the margin areas including the invaded areas, the OAR, the PRV, the dose distribution, the differences between the planned dose values and the expected dose values, the over exposure areas, and the under exposure areas, on the display unit 10B as a screen for editing the exposure conditions of the radiation such as the expected dose values typically.

When direction information for changing the exposure conditions of the radiation has been input into the corresponding element, such as the dose calculation part 20 or the over/under exposure analysis part 21, from the input device 10A through the editing screen displayed on the display unit 10B, values, such as the dose distribution, are automatically calculated again based on new exposure conditions of the radiation according to the direction information. For example, if the information specifying the expected dose values or the tumor areas has been edited, the dose distribution is calculated again as the planned dose values since the expected dose values are set up for the respective tumor areas including the margins. That is, the dose calculation part 20 and the over/under exposure analysis part 21 update and display the information estimating the planned dose values based on the information for changing the expected dose values of the radiation input with reference to the information estimating the planned dose values displayed on the editing screen.

So far, the example of displaying the over exposure areas and the under exposure areas has been described. However, the over exposure time phases and the under exposure time phases may be also displayed as mentioned above. Namely, an image at each time phase at which at least one over exposure area exists can be determined as the over exposed time phase image while an image at each time phase at which at least one under exposure area exists can be determined as the under exposed time phase image.

Figure 10:
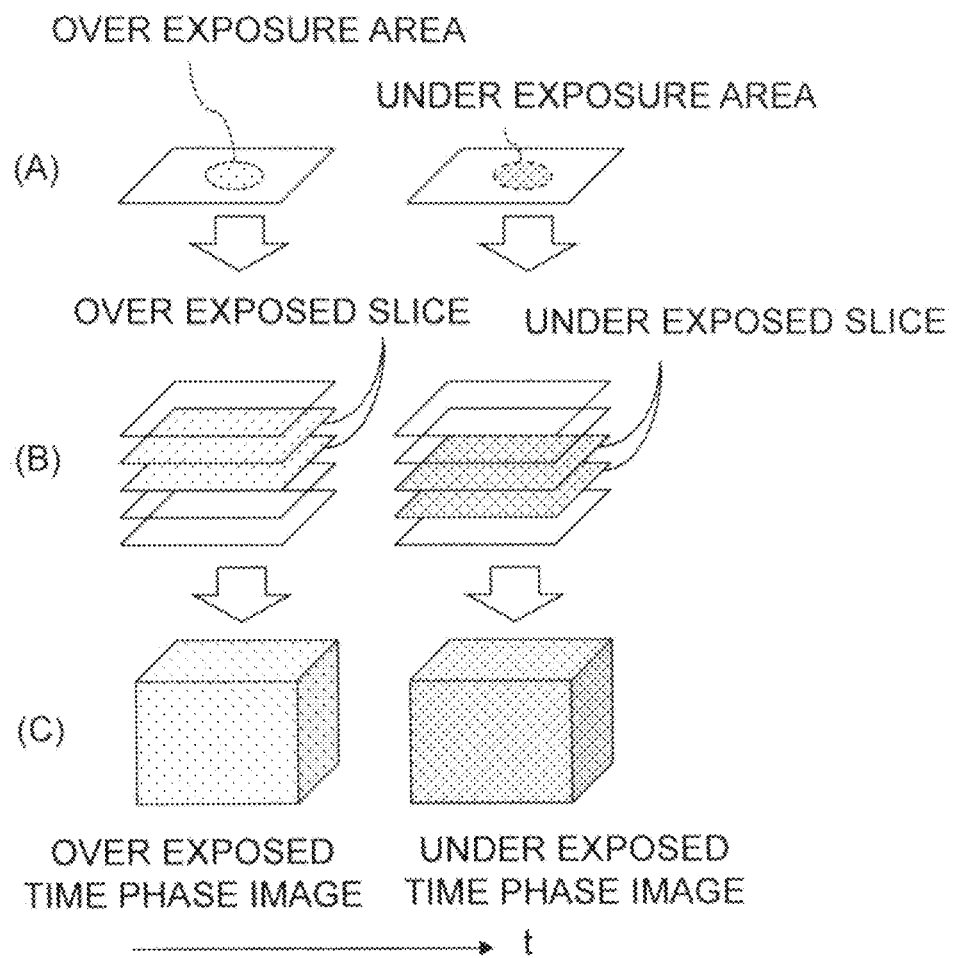
FIG. 10 is a diagram explaining an example of method of specifying over exposed time phase images and under exposed time phase images in the over/under exposure analysis part shown in FIG. 1.

FIG. 10 is a diagram explaining an example of method of specifying the over exposed time phase images and the under exposed time phase images in the over/under exposure analysis part 21 shown in FIG. 1.

As shown in FIG. 10 (A), each frame of slice image data on which at least one over exposure area exists can be specified. Similarly, each frame of slice image data on which at least one under exposure area exists can be specified. Each frame of the slice image data on which at least one over exposure area exists is defined as over exposed slice image data while each frame of the slice image data on which at least one under exposure area exists is defined as under exposed slice image data. Then, frames of the over exposed slice image data and frames of the under exposed slice image data can be specified in 3D volume image data as shown in FIG. 10 (B). Thereby, a piece of 3D volume image data at each time phase at which at least one frame of the over exposed slice image data exists can be specified as a piece of 3D over exposed time phase image data while a piece of 3D volume image data at each time phase at which at least one frame of the under exposed slice image data exists can be specified as a piece of 3D under exposed time phase image data.

When each time phase at which at least one over exposure area exists and each time phase at which at least one under exposure area exists have been specified, frames of diagnostic image data corresponding to mutually different time phases can be aligned in the time phase direction to be displayed in the time series with the time line. At this time, the frames of the diagnostic image data can be displayed so that degrees of the over exposures and the under exposures can be grasped.

Figure 11:
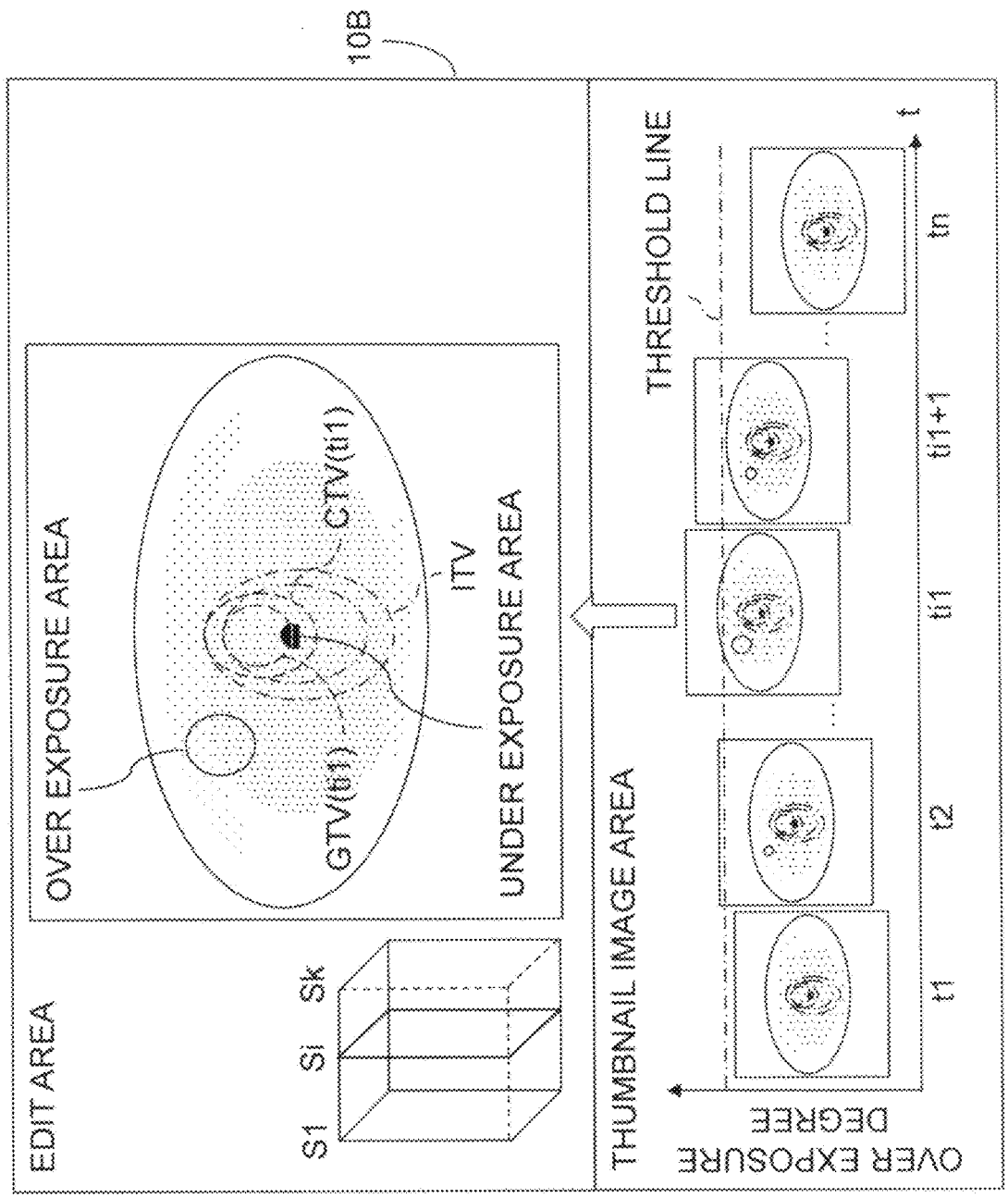
FIG. 11 is a diagram showing an example of displaying thumbnail images of diagnostic images in the time phase direction with the time line by the over/under exposure analysis part shown in FIG. 1 so that the degree in over exposure may be grasped to edit the expected dose value.

FIG. 11 is a diagram showing an example of displaying thumbnail images of diagnostic images in the time phase direction with the time line by the over/under exposure analysis part 21 shown in FIG. 1 so that the degree in over exposure may be grasped to edit the expected dose value.

As shown in FIG. 11, an editing area and a thumbnail image area can be displayed on the display unit 10B. In the thumbnail image area, diagnostic images at the time phases t1, t2, t3, . . . , tn at a same slice position can be aligned in the time phase direction to be displayed as thumbnail images. Moreover, in the thumbnail image area, the vertical axis representing the degree in over exposure is indicated in addition to the horizontal axis representing the time phase t which is the direction for aligning the thumbnail images. Then, each thumbnail image is indicated at a corresponding position in the vertical axis direction according to a degree in over exposure.

Therefore, the degrees in over exposure of the radiation can be grasped by viewing an indicated position of each thumbnail image. Furthermore, if a desirable range or an acceptable range in over exposure is indicated as a threshold line as shown in FIG. 11, each thumbnail image for which editing the expected dose values is needed can be checked easily. Note that, the degree in over exposure of the radiation may be expressed by a displaying method, such as displaying with colors, other than a way of changing a indicating position The degree in over exposure can be represented by an index related to other conditions, such as a kind of area, as well as the differences between the planned dose values and the expected dose values. For example, the differences between the planned dose values and the expected dose values in each invaded area can be estimated relatively small while those in each normal area, to which the over exposure is not desirable, can be estimated relatively big. In this case, a weighted additional value or the like of the differences between the planned dose values and the expected dose values between the areas can be used as the index representing the degree in over exposure. This is also the same for the degree in under exposure. That is, at least one of the over exposure areas, the under exposure areas, the over exposure time phases, and the under exposure time phases of the radiation can be calculated based on the kinds of areas defined for the tumor in addition to the differences between the planned dose values and the expected dose values of the radiation.

Moreover, when a thumbnail image is selected by operation of the input device 10A such as a mouse, the diagnostic image corresponding to the thumbnail image can be displayed on the editing area. Alternatively, a diagnostic image may be automatically displayed on the editing area in order of a time phase at which the differences between the planned dose values and the expected dose values are larger. FIG. 11 shows an example of displaying the diagnostic image, corresponding to the automatically selected thumbnail image at the time phase ti1 at which the degree in over exposure is the maximum, on the editing area.

In the editing area, a diagnostic image can be displayed with desired information which can be referred to effectively for editing exposure conditions of the radiation, such as the expected dose values. In the example shown in FIG. 11, the GTV (ti1) at the time phase ti1, the CTV (ti1) at the time phase ti1, the ITV, the differences between the planned dose values and the expected dose values, the over exposure areas, and the under exposure areas are overlapped and displayed on the diagnostic image.

Then, when an exposure condition of the radiation, such as the expected dose values, are changed through the diagnostic image displayed on the editing area, the estimation data including the over exposure areas and the under exposure areas is calculated again. Therefore, by repeating a selection of a thumbnail image and a change of the expected dose values or the like, the degrees in over exposure corresponding to the all thumbnail images can be made not more than the threshold line.

In addition, the slice positions of the displayed thumbnail images and diagnostic image may be also indicated. In the example shown in FIG. 11, it can be recognized that the slice Si has been chosen out of the slices from the slice S1 to the slice Sk.

Figure 12:
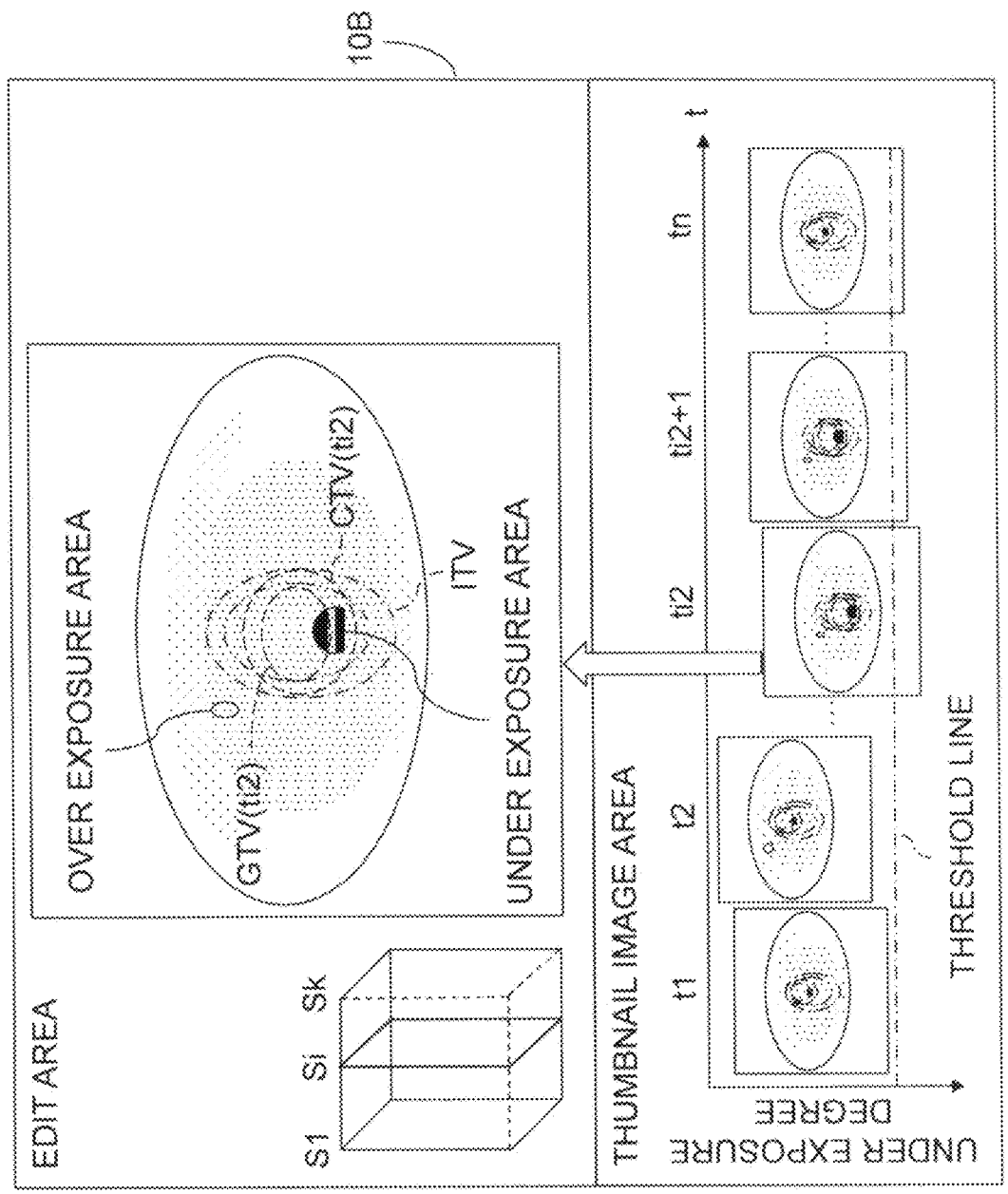
FIG. 12 is a diagram showing an example of displaying thumbnail images of diagnostic images in the time phase direction with the time line by the over/under exposure analysis part shown in FIG. 1 so that the degree in under exposure may be grasped to edit the expected dose value.

FIG. 12 is a diagram showing an example of displaying thumbnail images of diagnostic images in the time phase direction with the time line by the over/under exposure analysis part 21 shown in FIG. 1 so that the degree in under exposure may be grasped to edit the expected dose value.

Similarly to the example of screen on the display unit 10B shown in FIG. 11, the thumbnail images at the time phases t1, t2, t3, . . . , tn can be displayed on the thumbnail image area as shown in FIG. 12 so that the degrees in under exposure can be grasped. Namely, the thumbnail images can be arranged at 2D positions, each representing the time phase t and the degree in under exposure, with indicating a threshold line.

Moreover, the diagnostic image, corresponding to the time phase ti2 at which the degree in under exposure becomes the maximum, or the like can be selected. Then, the selected diagnostic image can be indicated in the editing area with the GTV (ti2) at the time phase ti2, the CTV (ti2) at the time phase ti2, the ITV, the differences between the planned dose values and the expected dose values, the over exposure areas, and the under exposure areas.

For the degree in under exposure, the differences between the planned dose values and the expected dose values in the GTV (ti2) and the CTV (ti2) can be estimated relatively big while those in the other areas can be estimated relatively small, for example. Thereby, the under exposure areas can be reduced in the GTV (ti2) and the CTV (ti2) to which it is desirable to expose a sufficient dose of the radiation.

Although the over exposure areas and the under exposure areas at a single slice position have been displayed in each of the examples shown in FIG. 8, FIG. 11, and FIG. 12, screen information allowing the grasp of the over exposure areas and under exposure areas corresponding to time phases at multi slice positions can also be created and displayed.

Figure 13:
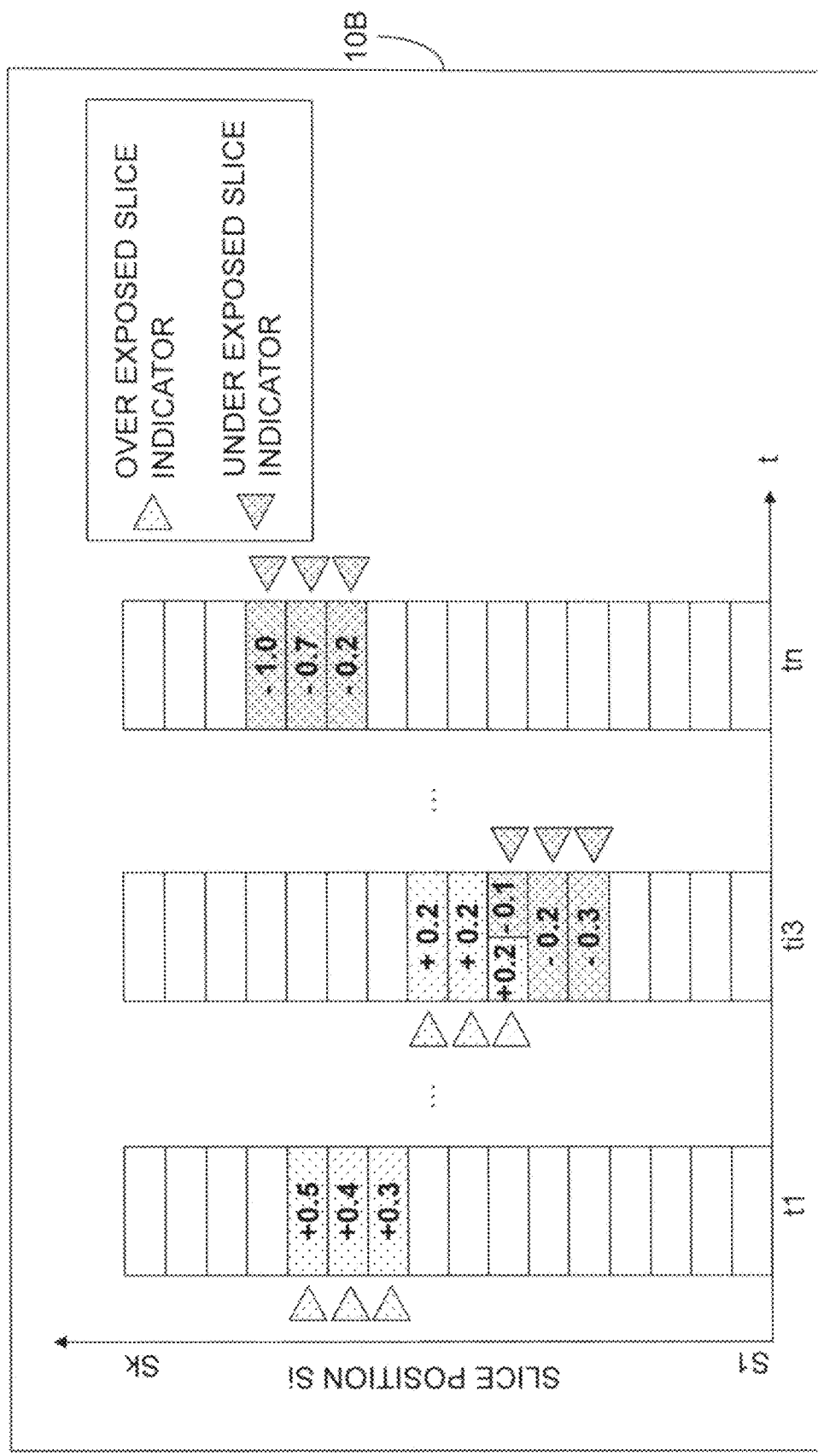
FIG. 13 is a diagram showing an example of displaying the existence of the over exposure areas and the under exposure areas corresponding to time phases at slice positions by the over/under exposure analysis part shown in FIG. 1.

FIG. 13 is a diagram showing an example of displaying the existence of the over exposure areas and the under exposure areas corresponding to time phases at slice positions by the over/under exposure analysis part 21 shown in FIG. 1.

As shown in FIG. 13, by using the vertical axis representing the slice position specified by the slice number Si (i=1, 2, 3, . . . , k) and the horizontal axis representing the time phase t (t1, t2, t3, . . . , tn), figures each expressing a slice image can be indicated two dimensionally on the screen of the display unit 10B. Then, each figure corresponding to the over exposed slice image on which at least one over exposure area exists, and each figure corresponding to the under exposed slice image, on which at least one under exposure area exists, can be emphasized and indicated with mutually different colors or the like so that they can be distinguished. Furthermore, an over exposure amount and/or an under exposure amount, which are the differences between the planned dose values and the expected dose values, can be also indicated in each figure representing a slice image.

However, as shown in FIG. 8, FIG. 11, and FIG. 12, both the over exposure area and the under exposure area exist on a frame of slice image in many cases actually. In this case, the slice image cannot be classified into either one of the over exposed slice image and the under exposed slice image.

Accordingly, an over exposed slice indicator, representing that the corresponding slice image is the over exposed slice image, and an under exposed slice indicator, representing that the corresponding slice image is the under exposed slice image, can be indicated so that they can point to a common slice image as shown in FIG. 13. Furthermore, both an over exposure amount and an under exposure amount can be indicated in the figure representing each slice image corresponding to both the over exposed slice image and the under exposed slice image, like the display of the slice image at the time phase ti3.

By such a schematic display method of slice images, each slice position at which at least one of the over exposure area and the under exposure area exists can be recognized easily. Moreover, when a figure of rectangle frame shown in FIG. 13 is selected by operation of the input device 10A, the detailed slice image corresponding to the selected figure may be displayed in the editing area as shown in FIG. 11 or FIG. 12.

Besides the above mentioned examples, diagnostic images corresponding to time phases may be indicated with the time line without specifying a slice position. For example, 3D images, such as VR images, to which a slice position is not specified or figures representing volume images can be indicated with aligning them in the time phase axis direction.

However, 3D images, such as volume images or VR images, may be also unable to be classified into either one of the over exposed time phase image and the under exposed time phase image. In that case, by displaying the over exposure indicator and the under exposure indicator as shown in FIG. 13 or displaying both the over exposure amount and the under exposure amount near each 3D image, each over exposed time phase image and each under exposed time phase image can be displayed so that they can be distinguished.

By the way, the time scale for display with the time line can be set to various temporal expressions in the radiotherapy. Therefore, the time scale may represent a temporal expression other than the time phase t in the above mentioned example. On the other hand, the positional scale may also represent a positional expression other than the slice position.

Figure 14:
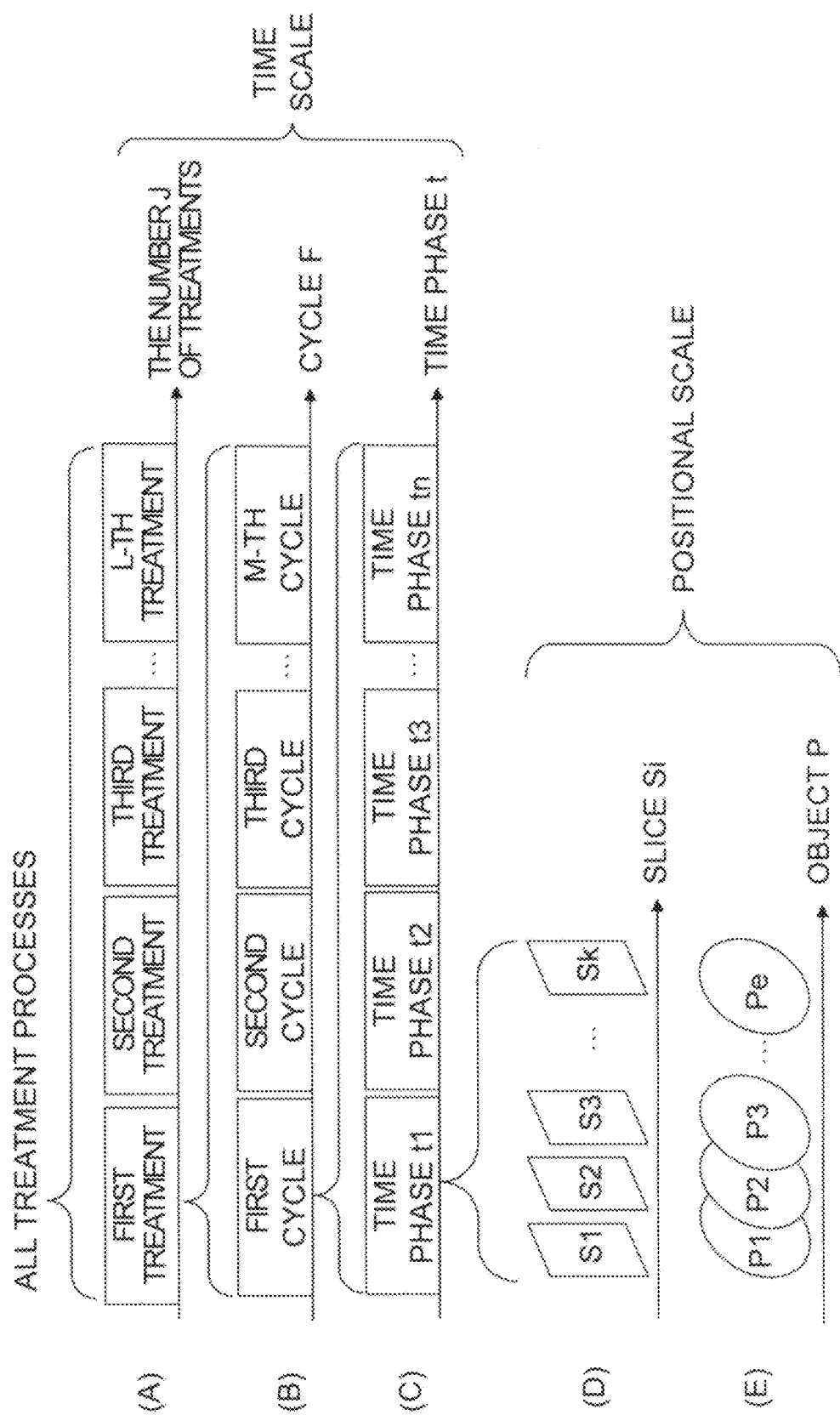
FIG. 14 is a diagram showing an example of scale expressions which can be used by the over/under exposure analysis part shown in FIG. 1 when images or figures are aligned to be displayed.

FIG. 14 is a diagram showing an example of scale expressions which can be used by the over/under exposure analysis part 21 shown in FIG. 1 when images or figures are aligned to be displayed.

As shown in FIG. 14 (A), all the processes of radiotherapy consist of two or more treatments. Therefore, images or figures representing images can be indicated with the time line of which time scale is the number J (J=1, 2, 3, . . . , L) of the treatments.

Moreover, one radiation treatment can be divided into cycles F (F=1, 2, 3, . . . , M) as a unit, as shown in FIG. 14 (B). In each cycle F, 4D image data is acquired. That is, one cycle F corresponds to one imaging. Therefore, the time scale may be the cycle F.

Furthermore, the 4D image data corresponding to one cycle consists of pieces of 3D image data at time phases t (t=t1, t2, t3, . . . , tn), as shown in FIG. 14 (C). Therefore, the time scale may be the time phase t.

Moreover, a piece of the 3D image data corresponding to a specific time phase t consists of frames of 2D slice image data, as shown in FIG. 14 (D). Accordingly, slice images may be aligned and displayed with the positional scale consisting of the slice positions specified by the slice numbers Si (i=1, 2, 3, . . . , k).

On the other hand, a piece of the 3D image data corresponding to a specific time phase t involves objects, including organs and the tumor areas, of which edges have been specified. Accordingly, 2D images or 3D images of areas in which the objects lie may be aligned and displayed with the positional scale consisting of representative positions of the objects identified by the object numbers P (P=P1, P2, P3, . . . , Pe).

Of course, the time scale or the positional scale in all the range may be displayed, or alternatively, the time scale or the positional scale extracted locally may be displayed. Moreover, choices of the meanings of the scale may be prepared so that a desired meaning can be selected from the choices.

On the other hand, the DVH calculation part 22 shown in FIG. 1 calculates the DVH, as needed. The DVH can be calculated based on the expected dose values of the radiation, the dose distribution calculated as the planned dose values, the PTV, and the PRV.

Figure 15:
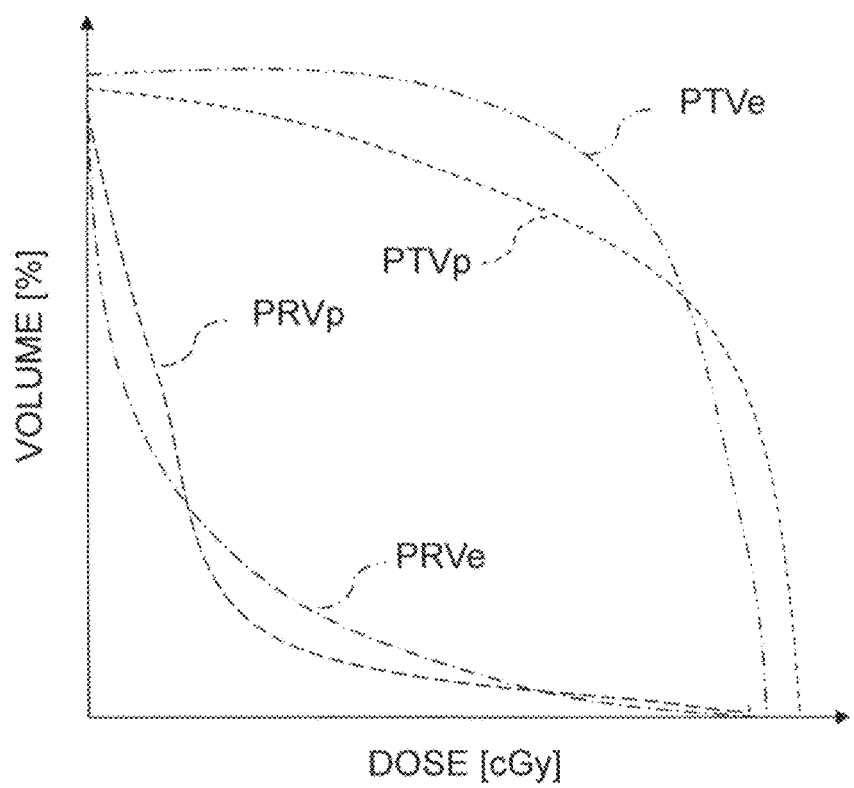
FIG. 15 is a graph which shows an example of DVH calculated by the DVH calculation part shown in FIG. 1.

FIG. 15 is a graph which shows an example of DVH calculated by the DVH calculation part 22 shown in FIG. 1.

In FIG. 15, the horizontal axis represents the planned doses [cGy] of the radiation while the vertical axis represents the volumes [%] to which the doses of the radiation shown by the horizontal axis are exposed. Moreover, in FIG. 15, the dashed-two dotted line represents the expected dose values PTVe of the radiation exposed to the PTV, the dotted line represents the planned dose values PTVp of the radiation exposed to the PTV, the dashed-dotted line represents the expected dose values PRVe of the radiation exposed to the PRV, and the dashed line represents the planned dose values PRVp of the radiation exposed to the PRV.

As shown in FIG. 15, the DVH is a graph showing the strengths of doses to the respective volumes of the PTV, as the area to be treated, and the PRV, as the normal tissues. Ideally, it is important to expose the radiation having a strong dose to the PTV since the PTV is the area to be treated. In contrast, it is important to minimize the dose of the radiation exposed to the PRV, which is the normal tissues, as far as possible.

Therefore, the dose to the PTV shows a convex curve in which the volume decreases nonlinearly along the increase in dose. Specifically, the expected dose values PTVe to the PTV show a curve which bends in the upper right as shown in FIG. 15. On the contrary, the dose to the PRV shows a concave curve in which the volume decreases nonlinearly along the increase in dose. Specifically, the expected dose values PRVe to the PRV show a curve which bends in the lower left as shown in FIG. 15.

Then, the radiation having a sufficient dose can be exposed to the area to be treated by making the change rate of the planned dose values PTVp to the PTV local. Similarly, exposing the radiation having an excess dose can be avoided by making the change rate of the planned dose values PRVp to the PRV local.

However, increasing the dose to the PTV to approximate the planned dose values PTVp to the expected dose values PTVe leads to exposing the radiation having a strong dose to the PRV. That is, prioritizing the dose to the PTV results in exposing the radiation having an excess dose to the PRV. Conversely, decreasing the dose to the PRV to approximate the planned dose values PRVp to the expected dose values PRVe leads to exposing the radiation having a weak dose to the PTV. That is, prioritizing the dose to the PRV results in exposing the radiation having an insufficient dose to the PTV.

Therefore, it is important in the radiation treatment planning to appropriately balance the doses to the PTV and the PRV which have a trade-off relation. Accordingly, it is desired to display not only the above mentioned diagnostic image overlapped with the over exposure areas and the under exposure areas but the DVH. In that case, the DVH calculation part 22 indicates the calculated DVH as estimation information on the planned dose values on the screen of the display unit 10B together with the diagnostic image.

Figure 16:
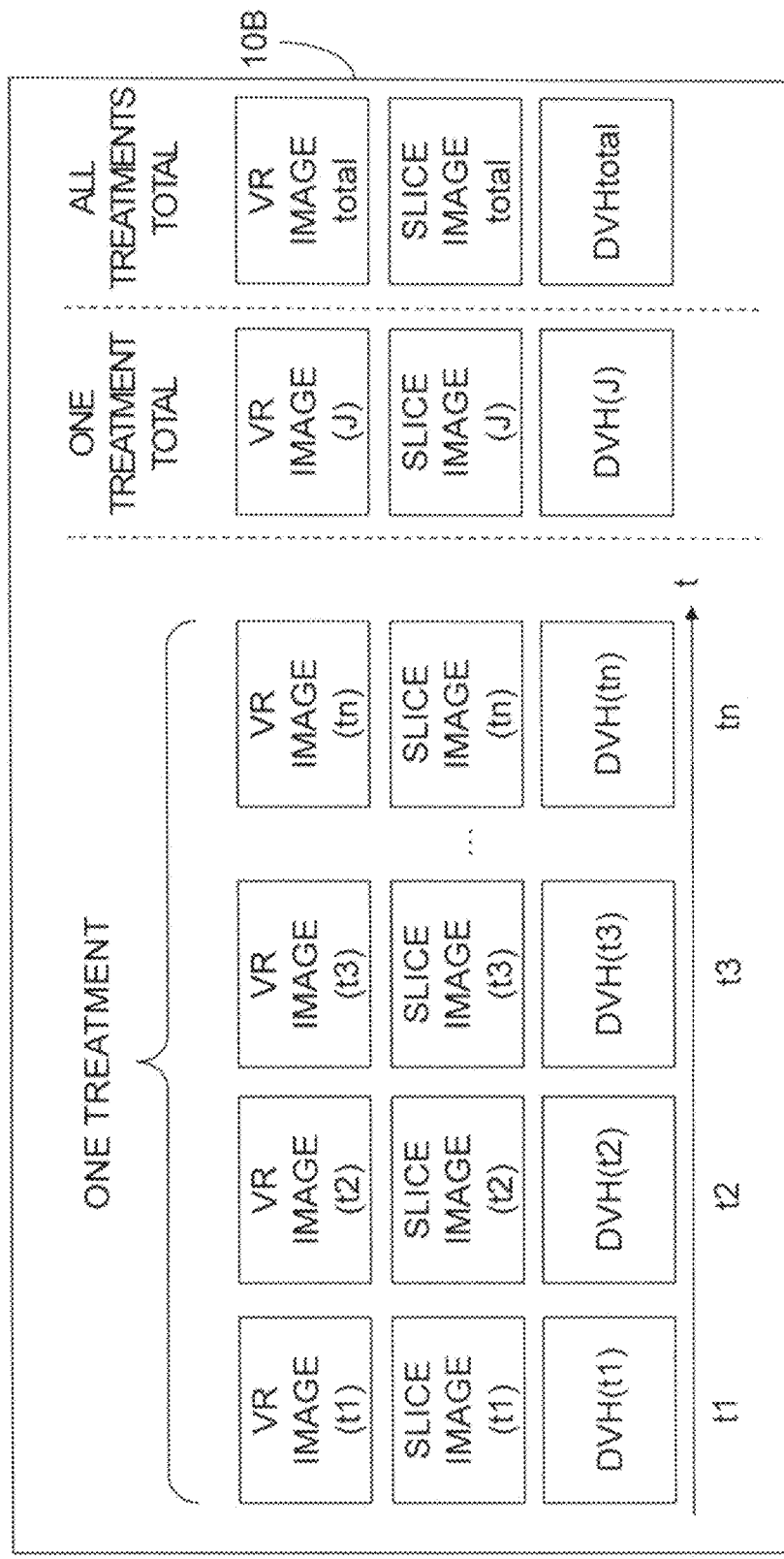
FIG. 16 is a diagram showing an example of displaying DVHs calculated by the DVH calculation part shown in FIG. 1 with diagnostic images.

FIG. 16 is a diagram showing an example of displaying DVHs calculated by the DVH calculation part 22 shown in FIG. 1 with diagnostic images.

As shown in FIG. 16, aligned DVHs can be indicated using an arbitrary positional scale or time scale with diagnostic images which correspond to the positions on the scale. FIG. 16 shows an example of indicating VR images, slice images, and DVHs at the time phases t (t1, t2, t3, . . . , tn) in parallel using the time scale representing the time phase t. Moreover, a VR image, a slice image, and a DVH representing the sum total of one treatment, and a VR image, a slice image, and a DVH representing the sum total of all the treatment processed may be also indicated.

Thus, the diagnostic images overlapped with the over exposure areas and the under exposure areas, and the DVHs can be displayed using various time scales and positional scales. Note that, the portions on the DVHs corresponding to the over exposure areas and the under exposure areas may be indicated emphatically so that they can be identified visually.

When such a radiation treatment planning including the calculation of the dose distribution by the initial input of the expected dose values and the edit of the input expected dose values has been completed, the radiation treatment along the treatment planning becomes possible. Then, the radiation treatment based on the treatment planning is performed by the radiation treatment apparatus 3 as shown in FIG. 2.

That is, the above mentioned radiotherapy information generation apparatus 1 is an apparatus configured to specify areas, such as the CTV and the invaded area, defined with regard to the tumor analytically by image processing of diagnostic image data. Furthermore, the radiotherapy information generation apparatus 1 is an apparatus configured to automatically calculate a dose distribution of the radiation as planned dose values based on expected dose values and the specified respective tumor areas to display estimation information including over exposure areas of the radiation, under exposure areas, over exposure time phases, under exposure time phases, and DVHs with differences between the expected dose values and the planned dose values.

Therefore, according to the radiotherapy information generation apparatus 1, the areas, such as the CTV and the invaded area, defined with regard to the tumor can be calculated quantitatively. Moreover, the organ to be treated can be also extracted by image processing of diagnostic images. As a result, the accuracy for extracting the organ can be improved to reduce the error in the GTV. Furthermore, the invaded areas can be specified analytically and quantitatively. Therefore, the accuracy for extracting the invaded areas can be improved to reduce the error in the CTV.

On the other hand, the moving range of organ can be also calculated analytically based on a result of motion analysis. Thereby, the accuracy in the IM, corresponding to a movable range of the organ, and the ITV can be also improved.

In addition, estimation information, such as the over exposure areas of the radiation, the under exposure areas, the over exposure time phases, the under exposure time phases, and the DVHs, calculated based on the respective kinds of tumor areas including the quantitatively specified invaded areas by the tumor can be visually displayed with diagnostic images. As a result, it becomes possible to grasp the dose planning intuitively. Furthermore, the dose planning can be edited easily to reduce over and under exposures of the radiation.

MODIFICATION

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, in the above mentioned embodiment, the explanation has been made for the example where elements such as the GTV calculation part 12, the invasion analysis part 13, the CTV calculation part 14, the temporal change analysis part 15, the ITV calculation part 16, the PTV calculation part 17, the OAR extraction part 18, and the PRV calculation part 19 of the radiotherapy information generation apparatus 1 function as a region specific unit configured to specify at least one area, such as the GTV and an invaded area of the tumor, defined with respect to a tumor by analysis processing of diagnostic image data while the dose calculation part 20 and the over/under exposure analysis part 21 function as a planning estimation unit configured to display estimation information of planned dose values calculated based on the area and expected dose values of a radiation. However, a radiotherapy information generation apparatus shown by another functional block diagram may be configured as long as the functions as the region specific unit and the planning estimation unit are provided.

What is claimed is:

1. A radiotherapy information generation apparatus comprising:
a computer configured to:
automatically specify at least one area defined with respect to a tumor by analysis processing of diagnostic image data, the analysis processing including threshold processing of the diagnostic image data, the diagnostic image data comprising first image data and second image data captured by different modalities, the at least one area including an invaded area of the tumor, the diagnostic image data allowing automatically specifying the invaded area by an invaded area threshold processing of the threshold processing, the invaded area threshold processing comprising identifying pixels having values less than a first threshold in the first image data and having values less than a second threshold in the second image data as belonging to the invaded area, the invaded area being an area inside a Clinical Target Volume (CTV) and outside of and excluding an area inside of a Gross Tumor Volume (GTV), the invaded area being automatically specified by the first threshold processing of the diagnostic image data, the GTV being automatically specified by a tumor area threshold processing of the threshold processing of the diagnostic image data, the tumor area threshold processing comprising identifying pixels having values greater than the first threshold in the first image data and having values less than the second threshold in the second image data as belonging to the GTV, the GTV being defined as a tumor portion which can be recognized visually on the diagnostic image data, the CTV being automatically specified by adding the invaded area to the GTV, the CTV being defined as the GTV and the invaded area which cannot be recognized with a naked eye on the diagnostic image data;
automatically calculate at least one of differences between planned dose values and expected dose values, an over exposure area, an under exposure area, an over exposure time phase, and an under exposure time phase of a radiation, based on the expected dose values and the at least one area including the invaded area, as estimation information of the planned dose values; and
display the estimation information of planned dose values calculated based on the area and expected dose values of a radiation.

2. A radiotherapy information generation apparatus of claim 1,
wherein said computer is configured to calculate at least one of the over exposure area, the under exposure area, the over exposure time phase and the under exposure time phase of the radiation based on a kind of the area defined with respect to the tumor and the differences between the planned dose values and the expected dose values of the radiation.

3. A radiotherapy information generation apparatus of claim 1,
wherein said computer is configured to update and display the estimation information based on change information of the expected dose values of the radiation input with reference to the estimation information.

4. A radiotherapy information generation apparatus of claim 1,
wherein said computer is configured to specify at least one of an internal target volume defined with respect to the tumor and a margin area in a consideration of a movement of an organ, based on a result of projection processing or a movement analysis.

5. A radiotherapy information generation apparatus of claim 1,
wherein said computer is configured to specify the invaded area of the tumor based on a combination of PET image data and X-ray CT image data or a combination of fractional anisotropy and the PET image data.

6. A radiotherapy information generation apparatus of claim 1,
wherein said computer is configured to display a dose volume histogram, calculated based on the expected dose values of the radiation, a planning organ at risk volume and a planning target volume, as the estimation information.

7. A radiotherapy information generation apparatus of claim 1,
wherein said computer is configured to display estimation information of planned dose values calculated based on a gross tumor volume, the invaded area of the tumor, expected dose values of the radiation set to the gross tumor volume and expected dose values of the radiation set to the invaded area of the tumor.

8. A radiotherapy information generation apparatus comprising:
a computer configured to:
automatically specify a gross tumor volume and an invaded area of a tumor by analysis processing of diagnostic image data, the analysis processing including threshold processing of the diagnostic image data, the diagnostic image data comprising first image data and second image data captured by different modalities, the diagnostic image data allowing specifying the invaded area by an invaded area threshold processing of the threshold processing, the invaded area threshold processing comprising identifying pixels having values less than a first threshold in the first image data and having values less than a second threshold in the second image data as belonging to the invaded area, the invaded area being an area inside a Clinical Target Volume (CTV) and outside of and excluding an area inside of a Gross Tumor Volume (GTV), the invaded area being automatically specified by the first threshold processing of the diagnostic image data, the GTV being automatically specified by a tumor area threshold processing of the threshold processing of the diagnostic image data, the tumor area threshold processing comprising identifying pixels having values greater than the first threshold in the first image data and having values less than the second threshold in the second image data as belonging to the GTV, the GTV being defined as a tumor portion which can be recognized visually on the diagnostic image data, the CTV being automatically specified by adding the invaded area to the GTV, the CTV being defined as the GTV and the invaded area which cannot be recognized with a naked eye on the diagnostic image data; and
automatically calculate planned dose values based on the gross tumor volume, the invaded area of the tumor and expected dose values of a radiation.

9. A radiotherapy information generation apparatus of claim 8,
wherein said computer is configured to calculate the planned dose values based on expected dose values of the radiation set to each of the gross tumor volume and the invaded area of the tumor.

10. A radiotherapy information generation method comprising:
automatically specifying at least one area defined with respect to a tumor by analysis processing of diagnostic image data, the analysis processing including threshold processing of the diagnostic image data, the diagnostic image data comprising first image data and second image data captured by different modalities, the at least one area including an invaded area of the tumor, the diagnostic image data allowing automatically specifying the invaded area by an invaded area threshold processing of the threshold processing, the invaded area threshold processing comprising identifying pixels having values less than a first threshold in the first image data and having values less than a second threshold in the second image data as belonging to the invaded area, the invaded area being an area inside a Clinical Target Volume (CTV) and outside of and excluding an area inside of a Gross Tumor Volume (GTV), the invaded area being automatically specified by the first threshold processing of the diagnostic image data, the GTV being automatically specified by a tumor area threshold processing of the threshold processing of the diagnostic image data, the tumor area threshold processing comprising identifying pixels having values greater than the first threshold in the first image data and having values less than the second threshold in the second image data as belonging to the GTV, the GTV being defined as a tumor portion which can be recognized visually on the diagnostic image data, the CTV being automatically specified by adding the invaded area to the GTV, the CTV being defined as the GTV and the invaded area which cannot be recognized with a naked eye on the diagnostic image data;
automatically calculate at least one of differences between planned dose values and expected dose values, an over exposure area, an under exposure area, an over exposure time phase, and an under exposure time phase of a radiation, based on the expected dose values and the at least one area including the invaded area, as estimation information of the planned dose values; and
displaying the estimation information.

11. A radiotherapy information generation apparatus comprising:
a computer configured to:
automatically specify at least one area defined with respect to a tumor by analysis processing of diagnostic image data, the analysis processing including threshold processing of the diagnostic image data, the diagnostic image data comprising first image data and second image data captured by different modalities, the at least one area including an invaded area of the tumor, the diagnostic image data allowing automatically specifying the invaded area by an invaded area threshold processing of the threshold processing, the invaded area threshold processing comprising identifying pixels having values less than a first threshold in the first image data and having values less than a second threshold in the second image data as belonging to the invaded area, the invaded area being an area inside a Clinical Target Volume, (CTV) and outside of and excluding an area inside of a Gross Tumor Volume (GTV), the invaded area being automatically specified by the first threshold processing of the diagnostic image data, the GTV being automatically specified by a tumor area threshold processing of the threshold processing of the diagnostic image data, the tumor area threshold processing comprising identifying pixels having values greater than the first threshold in the first image data and having values less than the second threshold in the second image data as belonging to the GTV, the GTV being defined as a tumor portion which can be recognized visually on the diagnostic image data by the second threshold processing, the CTV being automatically specified by adding the invaded area to the GTV, the CTV being defined as the GTV and the invaded area which can be recognized visually by the first threshold processing;

automatically calculate at least one of differences between planned dose values and expected close values, an over exposure area, an under exposure area, an over exposure time phase, and an under exposure time phase of a radiation, based on the expected dose values and the at least one area including the invaded area, as estimation information of the planned dose values; and display the estimation information of planned dose values calculated based on the area and expected dose values of a radiation.

12. A radiotherapy information generation apparatus of claim 11, wherein said computer is configured to calculate at least one of the over exposure area, the under exposure area, the over exposure time phase and the under exposure time phase of the radiation based on a kind of the area defined with respect to the tumor and the differences between the planned dose values and the expected dose values of the radiation.

13. A radiotherapy information generation apparatus of claim 11, wherein said computer is configured to update and display the estimation information based on change information of the expected dose values of the radiation input with reference to the estimation information.

14. A radiotherapy information generation apparatus of claim 11, wherein said computer is configured to specify at least one of an internal target volume defined with respect to the tumor and a margin area in a consideration of a movement of an organ, based on a result of projection processing or a movement analysis.

15. A radiotherapy information generation apparatus of claim 11, wherein said computer is configured to specify the invaded area of the tumor based on a combination of PET image data and X-ray CT image data or a combination of fractional anisotropy and the PET image data.

16. A radiotherapy information generation apparatus of claim 11, wherein said computer is configured to display a dose volume histogram, calculated based on the expected dose values of the radiation, a planning organ at risk volume and a planning target volume, as the estimation information.

17. A radiotherapy information generation apparatus of claim 11, wherein said computer is configured to display estimation information of planned dose values calculated based on a gross tumor volume, the invaded area of the tumor, expected dose values of the radiation set to the gross tumor volume and expected dose values of the radiation set to the invaded area of the tumor.

\* \* \* \* \*